US006450948B1

United States Patent
Matsuura et al.

(10) Patent No.: US 6,450,948 B1
(45) Date of Patent: Sep. 17, 2002

(54) DEFLECTING TIP FOR SURGICAL CANNULA

(75) Inventors: David G. Matsuura, Escondido; Walter Dean Gillespie, La Mesa; Allen Newman, Rancho Santa Fe, all of CA (US)

(73) Assignee: Vista Medical Technologies, Inc., Carlsbad, CA (US)

( * ) Notice: Subject to any disclaimer, the term of this patent is extended or adjusted under 35 U.S.C. 154(b) by 0 days.

(21) Appl. No.: 09/433,603

(22) Filed: Nov. 2, 1999

(51) Int. Cl.$^7$ .................................................. A61B 1/00
(52) U.S. Cl. ............................ 600/139; 606/1; 600/146
(58) Field of Search ................................ 600/139, 143, 600/144, 146; 604/95.01, 94.04; 606/1

(56) References Cited

U.S. PATENT DOCUMENTS

| | | | |
|---|---|---|---|
| 944,830 A | 12/1909 | Sussmann | |
| 1,928,992 A | 10/1933 | Clark et al. | |
| 2,453,862 A | 11/1948 | Salisbury | |
| 3,060,972 A | 10/1962 | Sheldon | |
| 4,198,960 A | * 4/1980 | Utsugi | 600/146 |
| 4,353,358 A | * 10/1982 | Emerson | 600/146 |
| 4,580,551 A | 4/1986 | Siegmunc | |
| 4,686,963 A | * 8/1987 | Cohen et al. | 600/146 |
| 4,904,048 A | 2/1990 | Sogawa et al. | |
| 4,934,340 A | 6/1990 | Ebling et al. | |
| 5,168,864 A | 12/1992 | Shockey | |
| 5,176,126 A | * 1/1993 | Chikama | 600/139 |
| 5,255,668 A | * 10/1993 | Umeda | 600/139 |
| 5,257,618 A | 11/1993 | Kondo | |
| 5,275,151 A | 1/1994 | Shocket et al. | |
| 5,307,803 A | 5/1994 | Matsuura et al. | |
| 5,318,041 A | 6/1994 | DuBois et al. | |
| 5,318,526 A | 6/1994 | Cohen | |
| 5,325,845 A | 7/1994 | Adair | |
| 5,335,647 A | 8/1994 | Brustad | |
| 5,409,453 A | 4/1995 | Lundquist et al. | |
| 5,423,807 A | 6/1995 | Milder | |
| 5,438,975 A | 8/1995 | Miyagi et al. | |
| 5,454,787 A | 10/1995 | Lundquist | |
| 5,487,757 A | * 1/1996 | Truckai et al. | 604/95.04 |
| 5,492,119 A | 2/1996 | Abrams | |
| 5,520,222 A | * 5/1996 | Chickama | 600/146 |
| 5,545,200 A | 8/1996 | West et al. | |
| 5,573,010 A | 11/1996 | Pflugbeil | |
| 5,656,011 A | 8/1997 | Uihlein et al. | |
| 5,662,606 A | * 9/1997 | Cimino et al. | 604/95.04 |
| 5,715,817 A | * 2/1998 | Stevens-Wright et al. | 604/95.04 |
| 5,876,373 A | 3/1999 | Giba et al. | |
| 5,906,590 A | 5/1999 | Hunjan et al. | |
| 5,921,915 A | 7/1999 | Aznoian et al. | |
| 5,931,811 A | 8/1999 | Haissaguerre et al. | |
| 5,935,102 A | 8/1999 | Bowden et al. | |
| 6,004,263 A | * 12/1999 | Nakaichi et al. | 600/120 |

FOREIGN PATENT DOCUMENTS

| | | |
|---|---|---|
| EP | 0 904 797 A2 | 3/1999 |
| WO | WO 97/27895 | 8/1997 |

\* cited by examiner

*Primary Examiner*—John P. Leubecker
(74) *Attorney, Agent, or Firm*—Fish & Richardson, P.C.

(57) ABSTRACT

A steerable probe with a deflectable tip. In one embodiment, the probe may include a cannula having a proximal end and a distal end and extending along a length therebetween, an exterior surface, an interior surface defining a lumen, an elongate flexible section extending along a first portion of the length and having a section proximal end and a section distal end. A pull wire for deflecting the flexible section in a first direction in a preferred bending plane may be substantially embedded in the cannula between the interior surface and the exterior surface and extending from the section proximal end to the section distal end. The pull wire may be secured to the cannula adjacent to the section distal end and freely passing through the section proximal end. Two longitudinal strengthening members may be embedded in and extend along the flexible section generally opposite each other about the preferred bending plane.

12 Claims, 23 Drawing Sheets

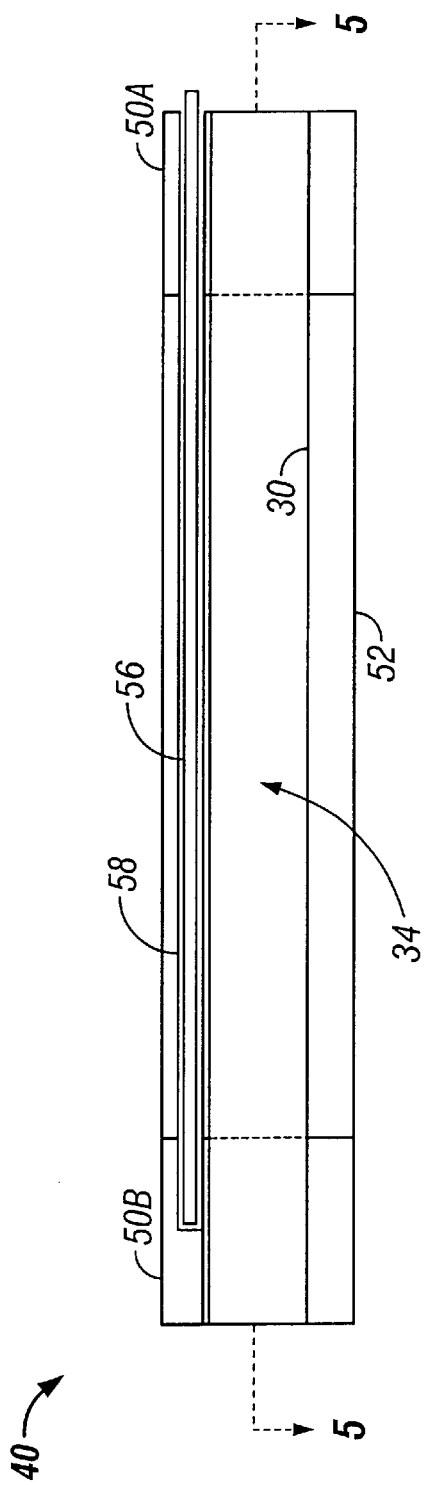
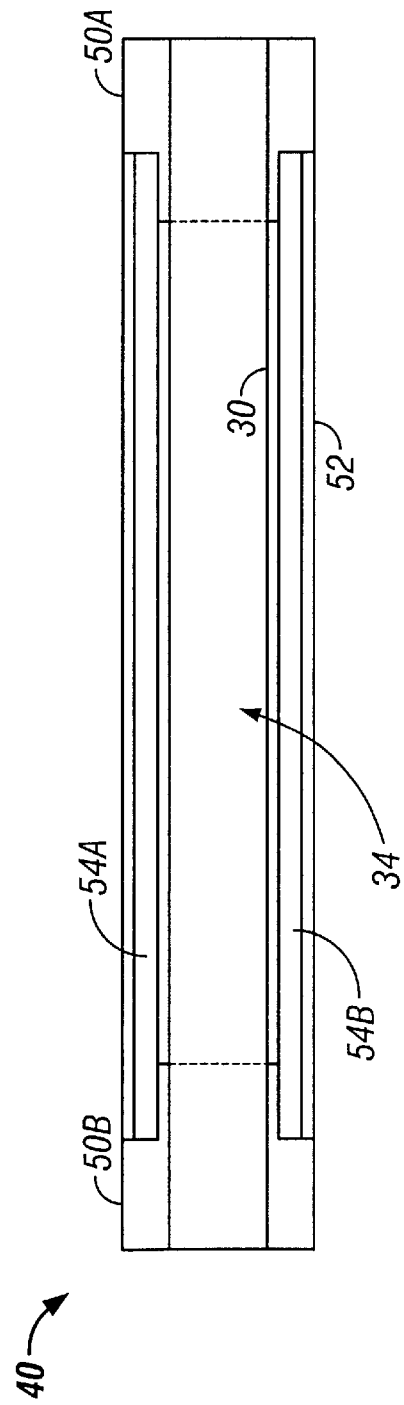
FIG. 4
FIG. 5

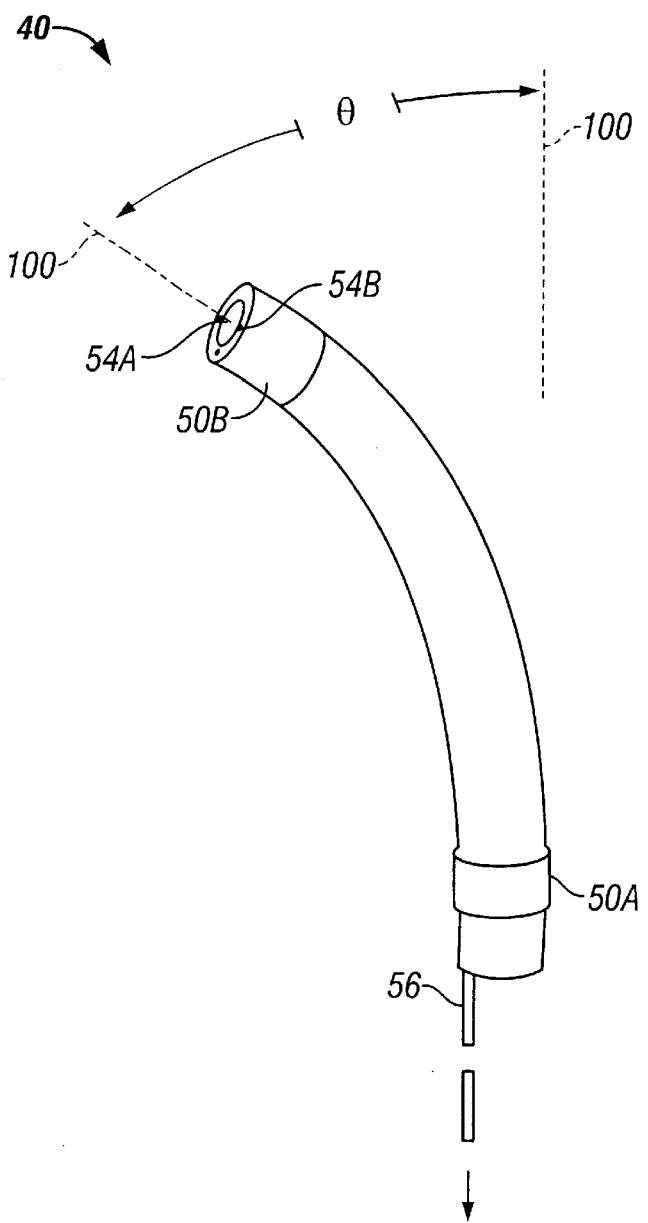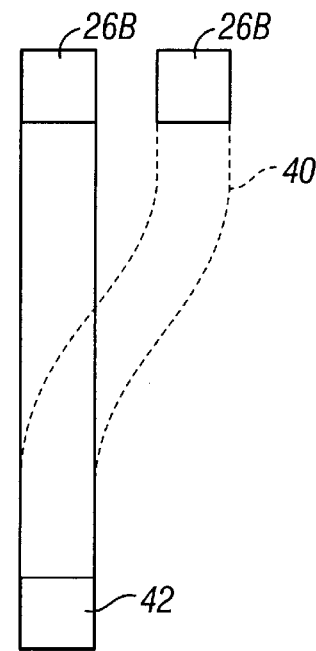
*FIG. 6*  *FIG. 10*

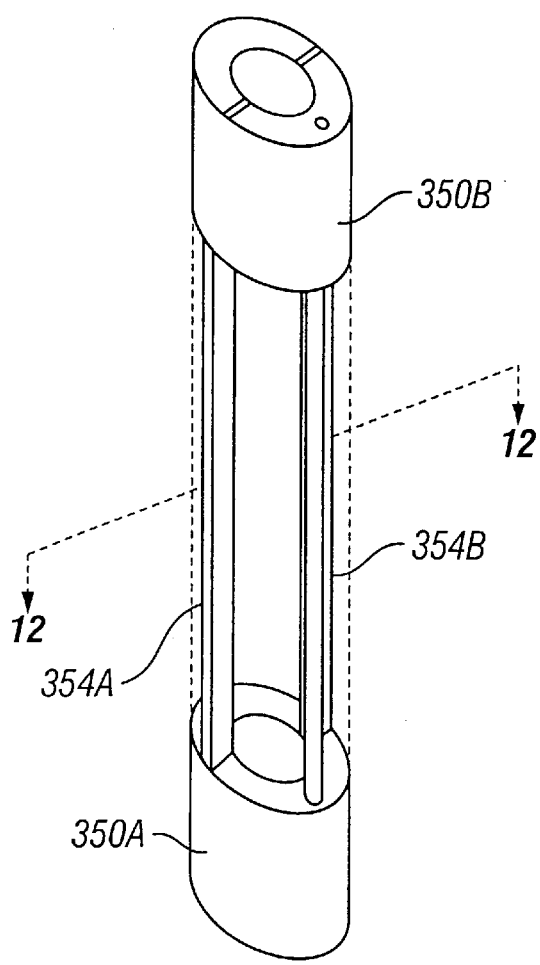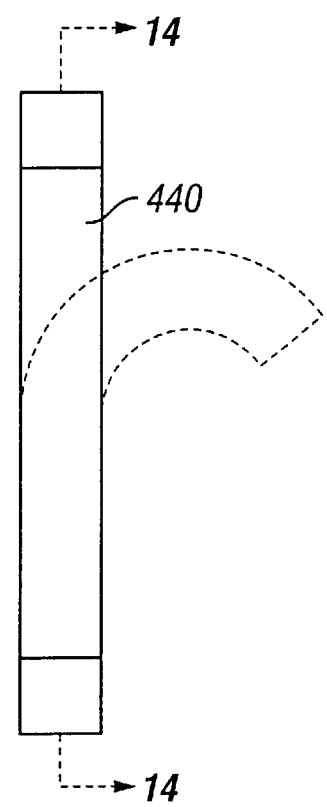
FIG. 11
FIG. 13

DEFLECTING TIP FOR SURGICAL CANNULA

TECHNICAL FIELD

This invention relates to steerable shafts, and more particularly to a hollow cannula tip which may be remotely steered (or deflected) by a user. Although preferred embodiments lie in the medical field, wherein the cannula may carry an endoscope or surgical tool, other uses are possible.

BACKGROUND

A variety of deflecting tip cannulae have been used or proposed for endoscopic or endosurgical use. In some such systems, such as that shown in U.S. Pat. No. 5,656,011 issued to Uihlein et al., the cannula is formed of a series of stacked, interlocking annular vertebrae. The vertebrae may be articulated via pulling on a tension spring band to flex the cannula from an initial, typically straight, configuration. Alternatively, with a preflexed cannula, a stiff sleeve may be extended and retracted over the cannula so that only the portion of the cannula distally beyond the sleeve is flexed.

U.S. Pat. No. 4,580,551 issued to Siegmund et al., discloses a cannula with a series of transverse slots or notches which serve to enhance flexibility of the cannula within a preferred bending plane. Articulation may be achieved via the use of four pull wires evenly disposed about the periphery of the cannula.

U.S. Pat. No. 5,307,803 issued to Matsuura et al., discloses an endoscope having a finned flexible member jacketed by a thin flexible tube. Channels defined by the fins contain one or more optical fibers and pull wires.

SUMMARY

The invention provides a steerable probe with a deflectable tip. In one embodiment, the probe may include a cannula having a proximal end and a distal end and extending along a length therebetween, an exterior surface, an interior surface defining a lumen, an elongate flexible section extending along a first portion of the length and having a section proximal end and a section distal end. A pull wire for deflecting the flexible section in a first direction in a preferred bending plane may be substantially embedded in the cannula between the interior surface and the exterior surface and extending from the section proximal end to the section distal end. The pull wire may be secured to the cannula adjacent to the section distal end, freely passing through the section proximal end. Two longitudinal strengthening members may be embedded in and extend along the flexible section generally opposite each other about the preferred bending plane. The invention also includes method of manufacturing such a structure.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 4 is a longitudinal sectional view of the cannula tip of FIG. 2, taken along line 4—4.

FIG. 5 is a longitudinal sectional view of the cannula tip of FIG. 4, taken along line 5—5.

FIG. 6 is a longitudinal view of the cannula tip of FIG. 2, in a deflected condition.

FIG. 10 is a longitudinal view of a cannula tip, with a racked condition shown in broken lines.

FIG. 11 is a view of an alternative cannula tip according to the invention.

FIG. 13 is a longitudinal view of an alternative cannula tip according to the invention, with a deflected condition shown in broken lines.

Like reference numbers and designations in the various drawings indicate like elements.

DETAILED DESCRIPTION

The invention provides a steerable probe for controllably positioning the end of the probe at a remote location by deflecting the tip of the probe. The tip of the probe is preferably flexible and deflectable using a pull wire, such as a stiff but bendable push rod. Strengthening members included in the probe preferably substantially reduce bending outside of the desired bending plane.

Figure 1:
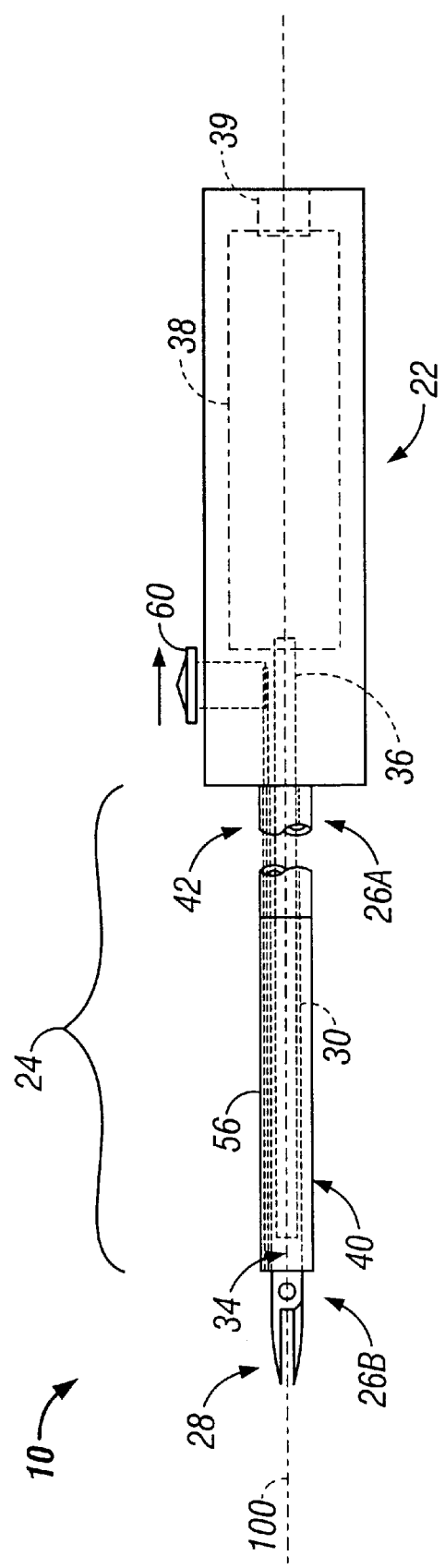
FIG. 1 is a side view, partially in phantom, of a surgical instrument having a steerable cannula tip according to the invention.

FIG. 1 is a side view, partially in phantom, of a surgical instrument having a steerable cannula tip according to the invention. A probe 10 includes a handle 22. A cannula 24 extends from a proximal end 26A, secured to the handle 22, to a distal end 26B. The cannula 24 has a central longitudinal axis 100. An instrument 28 (by way of example a cutter) is located at the distal end 26B of the cannula 24. The preferred cannula 24 has an interior surface 30 of generally circular section and an exterior surface 32 also of generally circular section. However, other cross-section shapes may be used. The interior surface 30 defines a lumen 34 extending the length of the cannula 24. The instrument 28 includes a linkage 36 extending through the lumen 34 to a control member 38 in the handle 22. The control member 38 may be connected to an external control interface 39. Alternatively, the control member 38 may be contained entirely within the probe 10.

The instrument 28 may alternatively be a surgical tool, such as a clamp or suction device, or an optical device, such as a camera, light, or laser. Alternatively, light may be supplied from an external device and supplied to the distal end 26B of the cannula 24 through an optical fiber element located in the lumen 34. In addition, multiple instruments, such as a surgical tool and an optical device, can be located at the distal end 26B of the cannula 24. In this case, the instruments may share the lumen 34, or control wires may extend through the cannula as well, similar to a pull wire 56 described below. Numerous applications are possible, both within and outside the medical field. The invention is useful for controlled placement and appropriate remote operation of small instruments.

The handle 22 may include additional control members, such as switches, buttons, dials, or slides. Controls for rotation of the cannula 24 may be provided. In the case of an instrument with multiple states, such as a cutter or clamp, controls for locking the instrument in such states may be included. In addition, the physical configuration of the handle 22 may vary depending upon the application. For example, a "pistol" shaped handle with a "trigger" control member 38 may be more convenient than a simple cylinder in surgical applications. In one such embodiment, the handle 22 is formed with a pistol grip and one or more triggers. The cannula 24 is configured to lock into place in the handle 22, such as with posts and locks in the handle 22. A release lever unlocks the cannula for removal. One trigger controls the deflection of the tip 40 through a pull wire 56, as described below. Additional triggers control the instrument 28, as appropriate, or provide additional deflection control. The handle 22 is preferably formed from a relatively rigid medical-grade plastic and may be discarded after one use or several uses.

The cannula 24 is preferably formed with a distal tip section 40 and a proximal base section 42. In the illustrated embodiment, the base section 42 is substantially rigid and the tip section 40 is flexible about a preferred plane. Manufacturing the cannula tip is described below.

Figure 2:
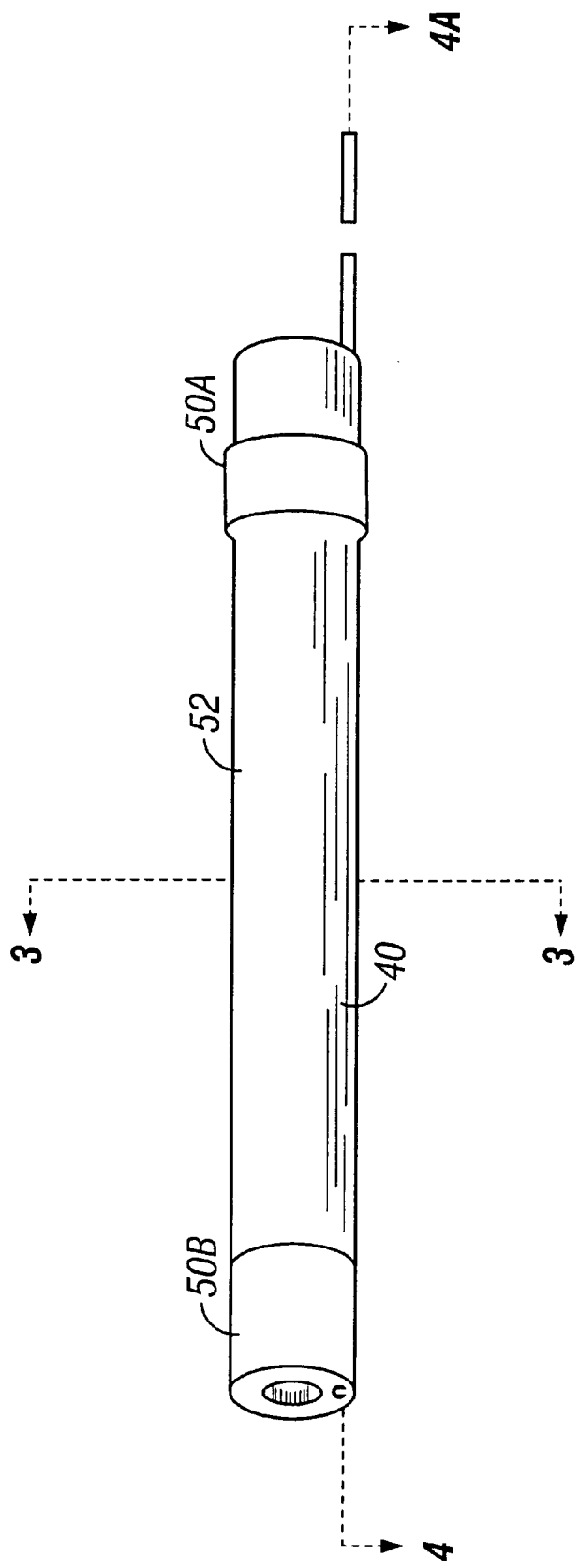
FIG. 2 is a longitudinal view of a steerable cannula tip according to the invention.

FIG. 2 is a longitudinal view of a steerable cannula tip according to the invention. The tip section 40 includes a proximal end collar 50A and a distal end collar 50B. The end collars 50A and 50B are preferably stiffeners which are substantially rigid and are connected together by a flexible tubular elastomeric body 52.

Figure 3:
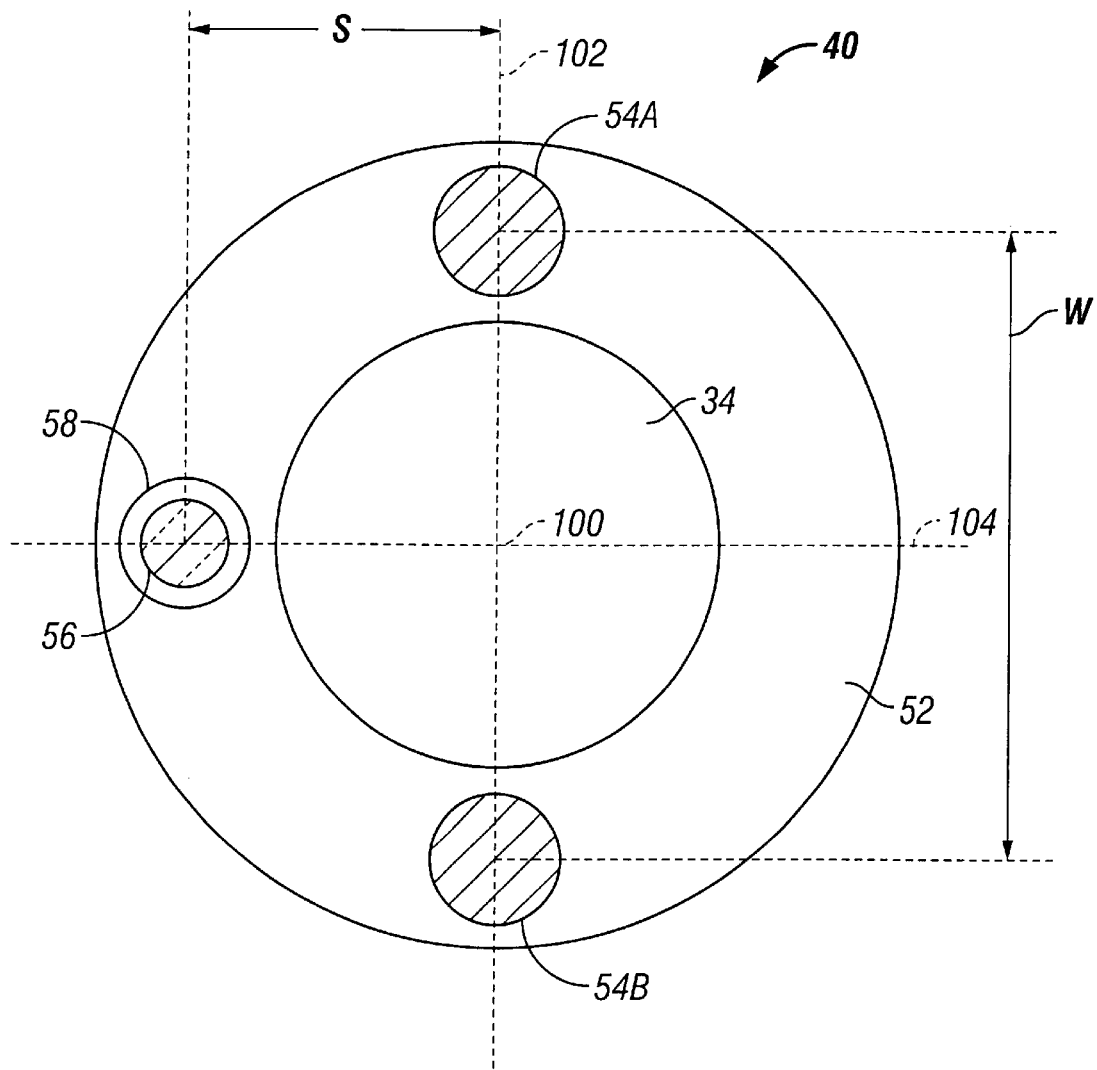
FIG. 3 is a transverse sectional view of the cannula tip of FIG. 2, taken along line 3—3.

FIG. 3 is a transverse sectional view of the cannula tip of FIG. 2, taken along line 3—3. A pair of longitudinal strengthening members 54A and 54B are formed or embedded in the body 52 between the interior and exterior surfaces of the body 52. Alternatively, each strengthening member may include multiple sub-members. The strengthening members extend substantially parallel to the longitudinal axis 100 of the cannula 24. In the illustrated embodiment, the strengthening members 54A and 54B are diametrically opposite each other about the longitudinal axis 100. The strengthening members 54A and 54B define a first plane 102 in which the strengthening members 54A and 54B reside. In the illustrated embodiment, the first plane 102 includes the longitudinal axis 100, but need not do so if the strengthening members 54A and 54B are not both aligned with the axis 100. A bending plane 104, perpendicular to the first plane 102, passes through the longitudinal axis 100. Also located between the interior and exterior surfaces of the body 52 is a longitudinal pull wire 56 located within a hollow sleeve 58. The pull wire 56 and sleeve 58 are located within the bending plane 104 on one side of the first plane 102.

FIG. 4 is a longitudinal sectional view of the cannula tip of FIG. 2, taken along line 4—4. The distal end of the pull wire 56 is secured to the distal collar 50B (for example, by gluing, friction fit, or interference fit). The pull wire 56 passes freely through the proximal collar 50A at the proximal end of the tip section 40. As shown in FIG. 1, the pull wire 56 passes through a channel in the wall of the base section 42, emerging in the actuator/handle 22 at the proximal end 26A of the cannula 24. The distal end of the pull wire 56 is coupled to an actuator 60, shown in FIG. 1, with which a user applies tension to the pull wire 56.

FIG. 5 is a longitudinal sectional view of the cannula tip of FIG. 4, taken along line 5—5. The distal and proximal ends of the strengthening members 54A and 54B are secured to, or integrally formed with, the distal and proximal collars 50B and 50A, respectively. For example, the strengthening members 54A and 54B may be molded of the same material, such as medical grade resin, as the distal and proximal collars 50A and 50B.

FIG. 6 is a longitudinal view of the cannula tip of FIG. 2, in a deflected condition. When a user applies tension to the pull wire 56, the tip section 40 flexes or deflects from the undeflected condition shown in FIG. 2 toward a deflected condition 40'. The tension in the pull wire 56 applies a responsive compressive force to the remainder of the cannula 24. This compressive force is transmitted from the distal collar 50B, through the longitudinal strengthening members 54A and 54B, to the proximal collar 50A, and therefrom through the rigid base section 42 to the actuator/handle 22. The strengthening members' 54A and 54B resistance to compression prevents the tip section 40 from collapsing.

More particularly, with the tip section 40 in an initial undeflected configuration, a tensile force T applied to the pull wire 56 acts on a lever arm S which is the separation between the pull wire 56 and the plane 102, as shown in FIG. 3. The resulting bending moment τ is the product of T and S. The moment τ causes a responsive bending of the cannula 24 as previously described. One characteristic measurement of the deflection is the angle θ (shown in FIG. 6) between the axis 100' defined by the distal end 26B of the cannula 24 in the deflected condition 40' and the axis 100 in the undeflected condition.

The location of the strengthening members 54A and 54B diametrically opposite each other substantially maximizes their separation W (see FIG. 3). The separation W will generally determine the ability of the tip section 40 to resist bending transverse to the bending plane 104. A torque which would otherwise cause such bending will place one of the longitudinal strengthening members under compression while placing the other under tension. Thus, the ability of the longitudinal strengthening members 54A and 54B to resist strain in both tension and compression is desirable to avoid bending transverse to the bending plane 104.

For a given angle of deflection, the length of the flexible section is preferably proportional to the radius of curvature of the deflected section. Thus, to accommodate different environments it may be desirable to provide a number of alternative lengths for the flexible section depending upon the desired relation between the degree of deflection and the radius of curvature.

Figure 7:
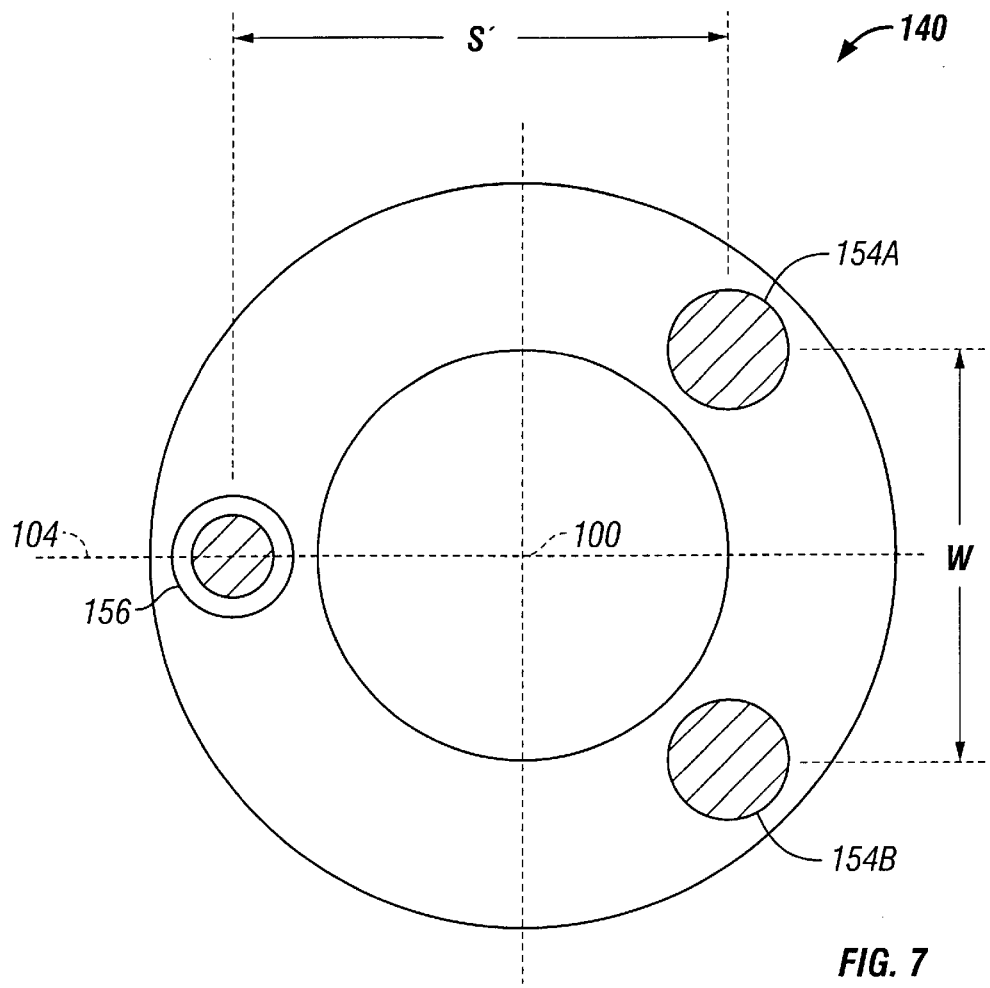
FIG. 7 is a transverse sectional view of an alternative cannula tip according to the invention.

FIG. 7 shows a section of an alternative flexible cannula tip 140. The tip 140 includes a pair of longitudinal strengthening members 154A and 154B which do not define a plane that includes the axis 100. Rather, both 154A and 154B are located on a side of the cannula 140 opposite a pull wire 156, and define a plane spaced from the axis 100. Such an embodiment may provide a relatively larger lever S' than the lever S of the embodiment of FIGS. 2–6. This reduces the tensile force T which must be applied to the pull wire 156 to induce a given deflection. A trade-off arises in that the reduced separation W' reduces the resistance of the cannula 140 to bending outside of the bending plane 104 (transverse to the bending plane).

Figure 8:
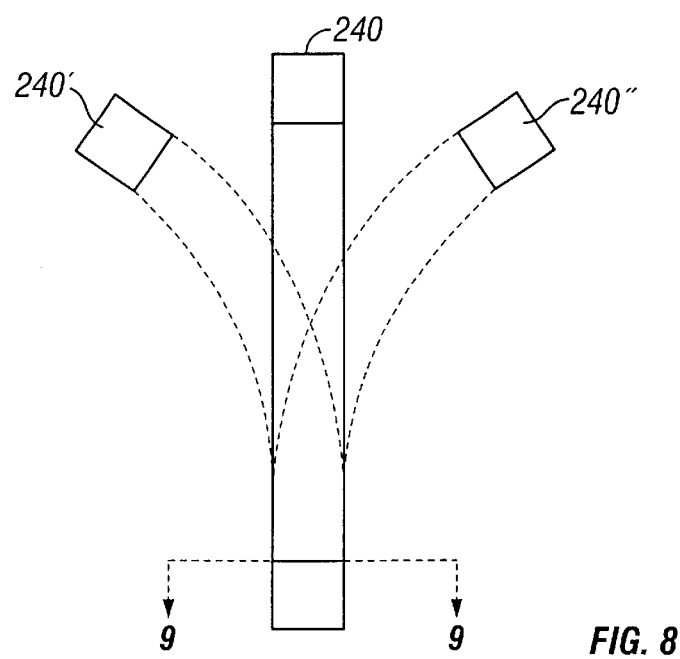
FIG. 8 is a longitudinal view of an alternative cannula tip according to the invention, with deflected conditions shown in broken lines.
Figure 9:
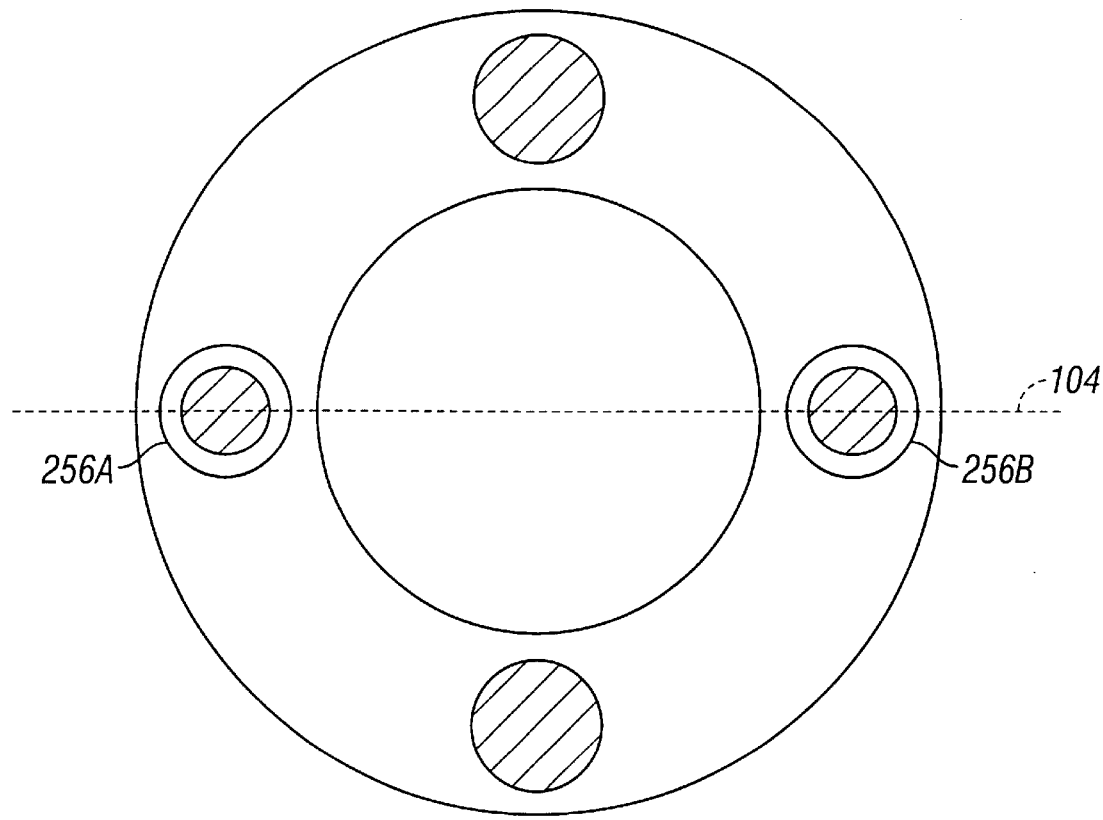
FIG. 9 is a transverse sectional view of the cannula tip of FIG. 8, taken along line 9—9.

FIG. 8 is a longitudinal view of an alternative cannula tip 240 with deflected conditions shown in broken lines. The cannula tip 240 has a range of motion extending from a first deflected condition 240' to a second deflected condition 240". The respective conditions 240' and 240" represent deflections to either side of a straight neutral position shown in solid line. FIG. 9 is a transverse sectional view of the cannula tip 240 of FIG. 8, taken along line 9—9. As shown in FIG. 9, this range of deflection may be achieved by providing a pair of diametrically opposed pull wires 256A and 256B, each of which may be similar to pull wire 56 of the embodiment of FIGS. 2–6. Tension applied to the pull wire 256A deflects the tip 240 toward the condition shown by 240' along the bending plane 104 and tension applied to the pull wire 256B deflects the tip 240 toward the condition shown by 240". Alternatively, such a range of deflection may be achieved with a single pull wire by preforming a tip in a curved condition such as that shown by condition 240". Tension applied to the pull wire will deflect the tip toward the straight condition and further increasing tension will deflect the tip toward the condition 240'.

An effect of a shear force applied to the tip transverse to the bending plane (aside from bending or deflecting transverse to the bending plane 104) is to cause "racking" of the tip. A cannula tip 40 in a racked condition is shown in broken lines in FIG. 10. With racking, the distal end 26B of the cannula remains parallel to its original neutral orientation but its position becomes laterally offset from the original position. To resist racking, the strengthening members may be formed so as to be resistant to deformation transverse to the bending plane 104.

Figure 12:
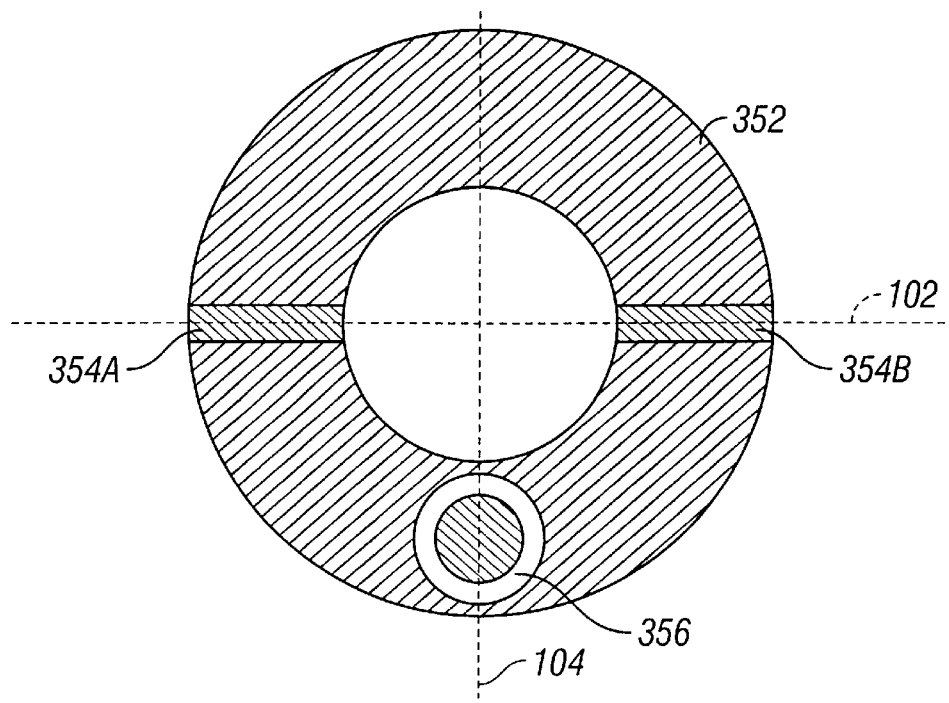
FIG. 12 is a transverse sectional view of the cannula tip of FIG. 11, taken along line 12—12.

One example of an anti-racking tip construction is shown in FIGS. 11 and 12. FIG. 11 is a view of an alternative cannula tip and FIG. 12 is a transverse sectional view of the cannula tip of FIG. 11, taken along line 12—12. In the illustrated embodiment, the longitudinal strengthening members 354A and 354B are formed as relatively wide flat slats (e.g., having a rectangular cross-section) within the transverse plane 102. This configuration makes the strengthening members resistant to deformation transverse to the bending plane 104. In the illustrated embodiment, the strengthening members 354A and 354B are unitarily formed with the proximal and distal collars 350A and 350B and are overmolded with an elastomeric body 352, as described below.

If it is desired for preferential bending to occur at particular places along the length of the cannula tip, the tip may be provided with increased flexibility in such locations.

Figures 14, 15:
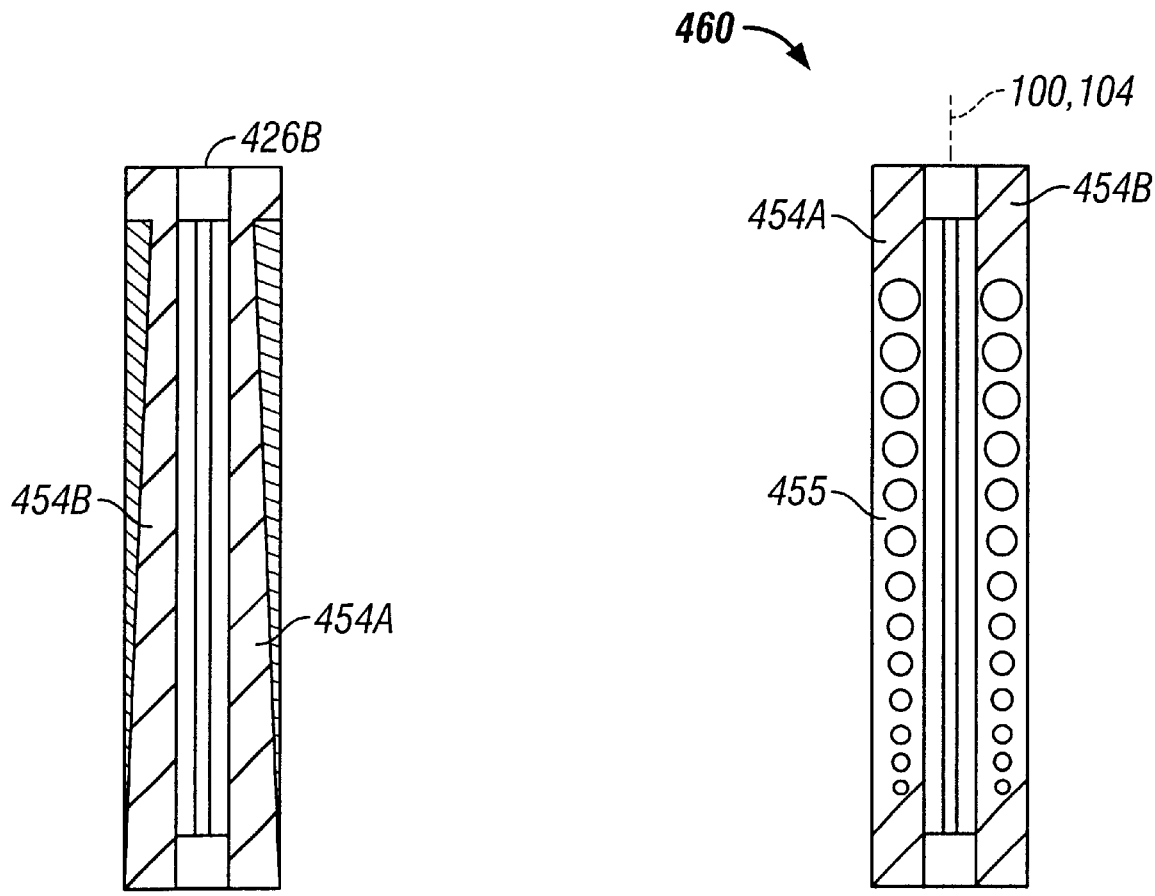
FIG. 14 is a longitudinal sectional view of the cannula tip of FIG. 13, taken along line 14—14.
FIG. 15 is a longitudinal sectional view of an alternative cannula tip according to the invention.

FIGS. 13 and 14 show a tip 440 formed for preferential flexing adjacent to its distal end 426B. FIG. 14 is a longitudinal sectional view of the cannula tip of FIG. 13, taken along line 14—14. This bending may be achieved by making the strengthening members 454A and 454B more flexible adjacent to the distal end than along the rest of the tip 440. In the illustrated embodiment, this variation in flexibility is achieved by providing the strengthening members 454A and 454B with a proximal-to-distal taper. Such tapering may also be used to offset the effects of friction between the pull wire and the sleeve in which it slides. Such friction reduces the tension in the pull wire in approximate proportion to the distance between the particular location of the friction on the wire within the tip and the proximal end of the tip. The result of such friction is that, absent compensation, deflection can be concentrated at the proximal end of the tip.

FIG. 15 is a longitudinal sectional view of an alternative cannula tip that provides varying flexibility along the length of the longitudinal strengthening members 454A and 454B. A tip 460 may include strengthening members 454A and 454B with a series of apertures 455 running approximately parallel to the plane 104. In addition to providing the desired flexibility profile, the apertures 455 allow the elastomeric body to be more firmly secured to the longitudinal strengthening members 454A and 454B by permitting infiltration of the elastomer into the apertures 455. Further, the portions of the body on either side of the strengthening members 454A and 454B may be connected to each other through the apertures 455. By progressively increasing the aperture size, with larger apertures being located distally, flexibility is increased at the distal end of the tip 460. Other patterns and arrangements may be used to create desired tip curvature upon deflection.

Figure 16:
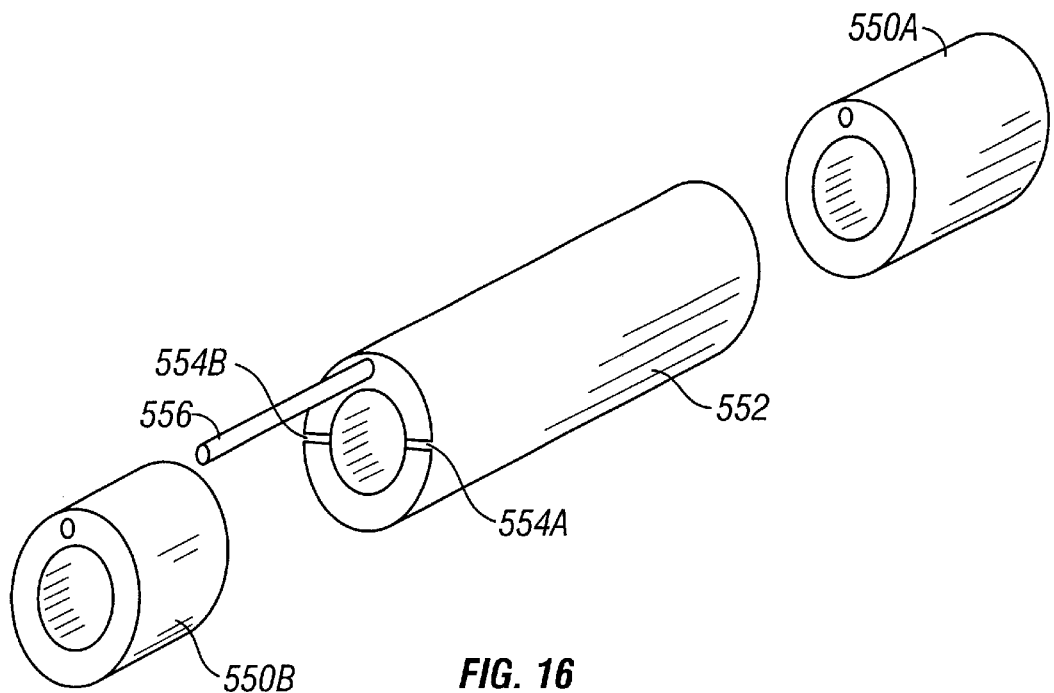
FIG. 16 is a partially exploded view of an alternative cannula tip according to the invention.

FIG. 16 shows a partially exploded view of an alternative cannula tip wherein the body 552 and longitudinal strengthening members 554A and 554B are coextruded as a single piece 555. The extruded piece 555 may be cut to a desired length. If not coextruded or conformed with the body 552 and strengthening members 554A and 554B, the pull wire 556 may be threaded through the proximal collar or end piece 550A, through the body 552, and then secured to the distal collar or end piece 550B. The collars may then be secured to the body such as by adhesive, heat bonding, solvent bonding, or mechanical interlocking.

Figure 17:
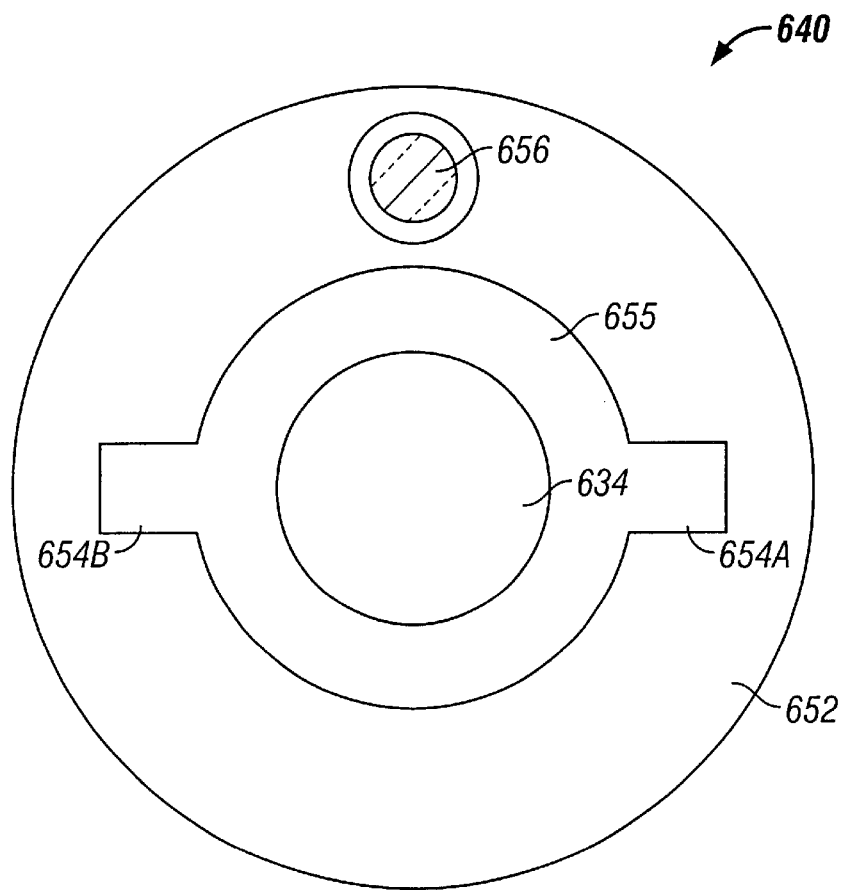
FIG. 17 is a transverse sectional view of an alternative cannula tip according to the invention.

FIG. 17 shows a transverse sectional view of another alternative body for a flexible tip section 640. In the illustrated embodiment, the longitudinal strengthening members 654A and 654B are formed with an inner sleeve 655 as a unitary body. The interior surface of the inner sleeve 655 forms the interior surface of the lumen 634. The integrated longitudinal strengthening members 654A and 654B and inner sleeve 655 may be formed of a relatively rigid material and preferably are embedded in an elastomeric outer sleeve 652. A pull wire 656 is positioned and function as in FIG. 3. This structure is preferably made by coextrusion, but may be formed by molding or machining the unitary body. An advantage of the structure is that the strengthening members 654A and 654B do not intrude into the lumen 634, and thus do not subtract from the cross-sectional area available for instruments.

Figure 18:
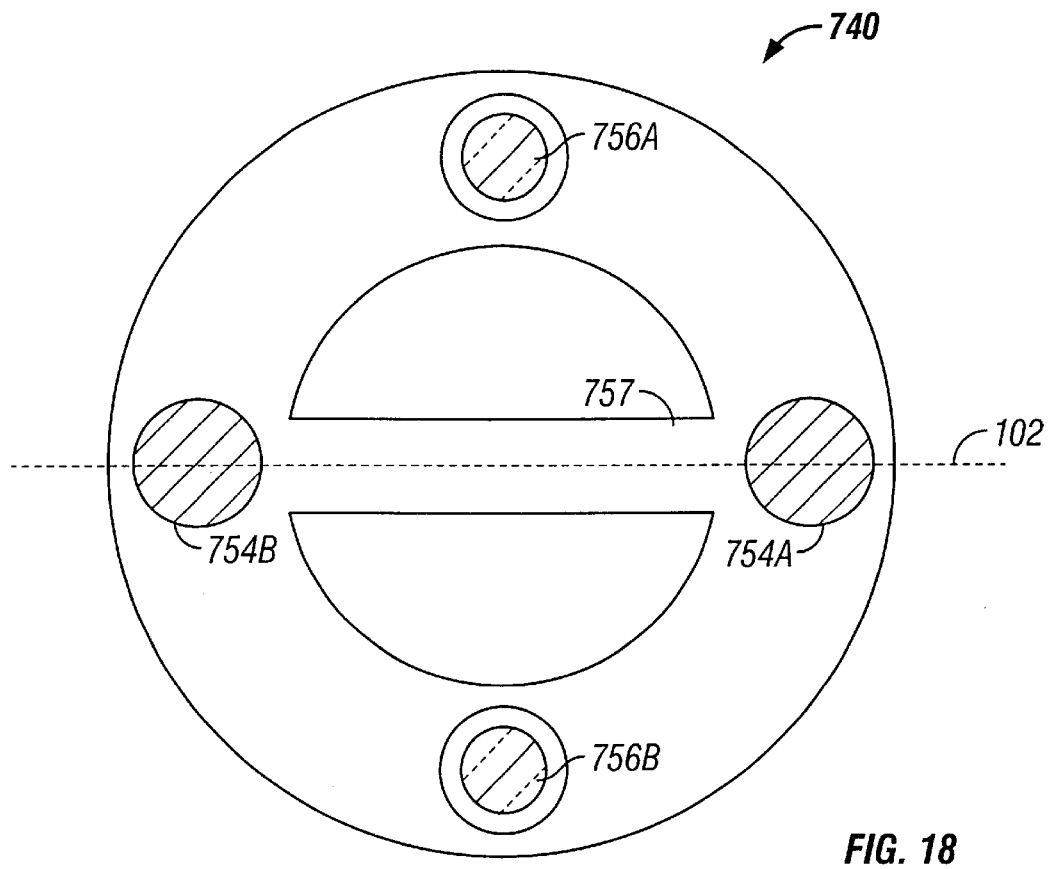
FIGS. 18–21 are transverse sectional views of alternative cannula tips according to the invention.

FIG. 18 shows a transverse sectional view of another alternative extruded or molded embodiment of a tip 740 formed with a web 757 extending along the plane 102 between the longitudinal strengthening members 754A and 754B. The web 757 defines a first lumen 734A and a second lumen 734B. First and second lumens 734A and 734B may be utilized, for example, for inlet and outflow of fluid. The tip 740 illustrated in FIG. 18 includes two pull wires 756A and 756B. Alternative tips may include a single pull wire, as described above.

Figure 19:
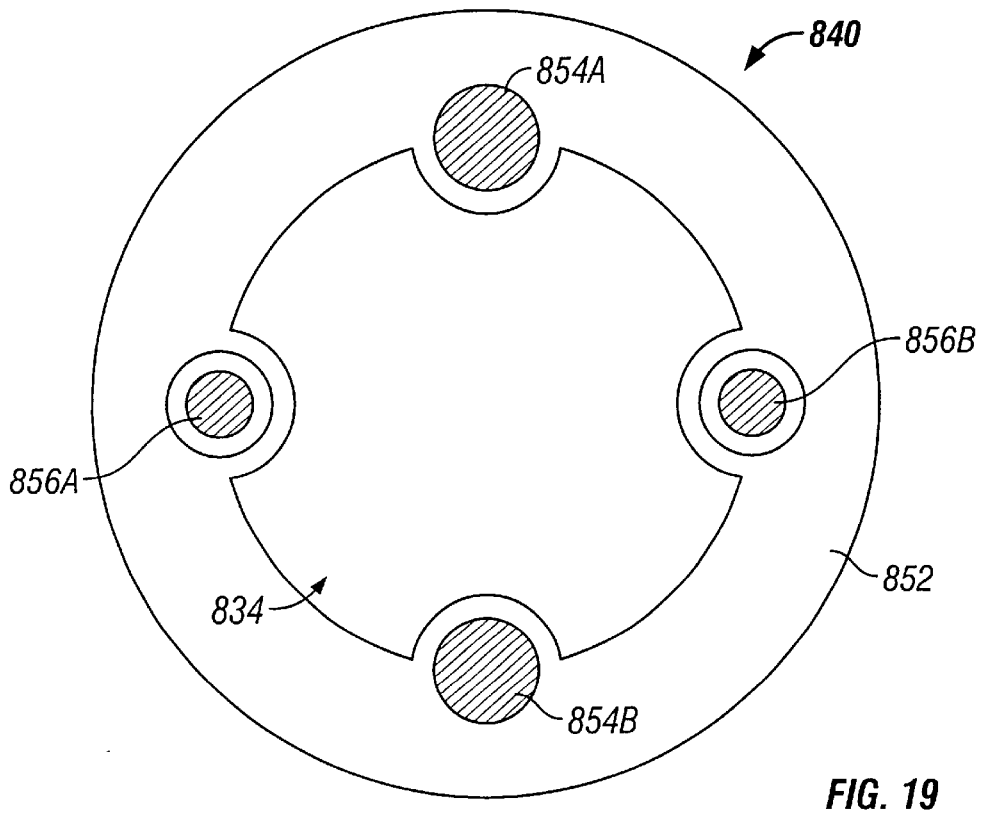
Figure 20:
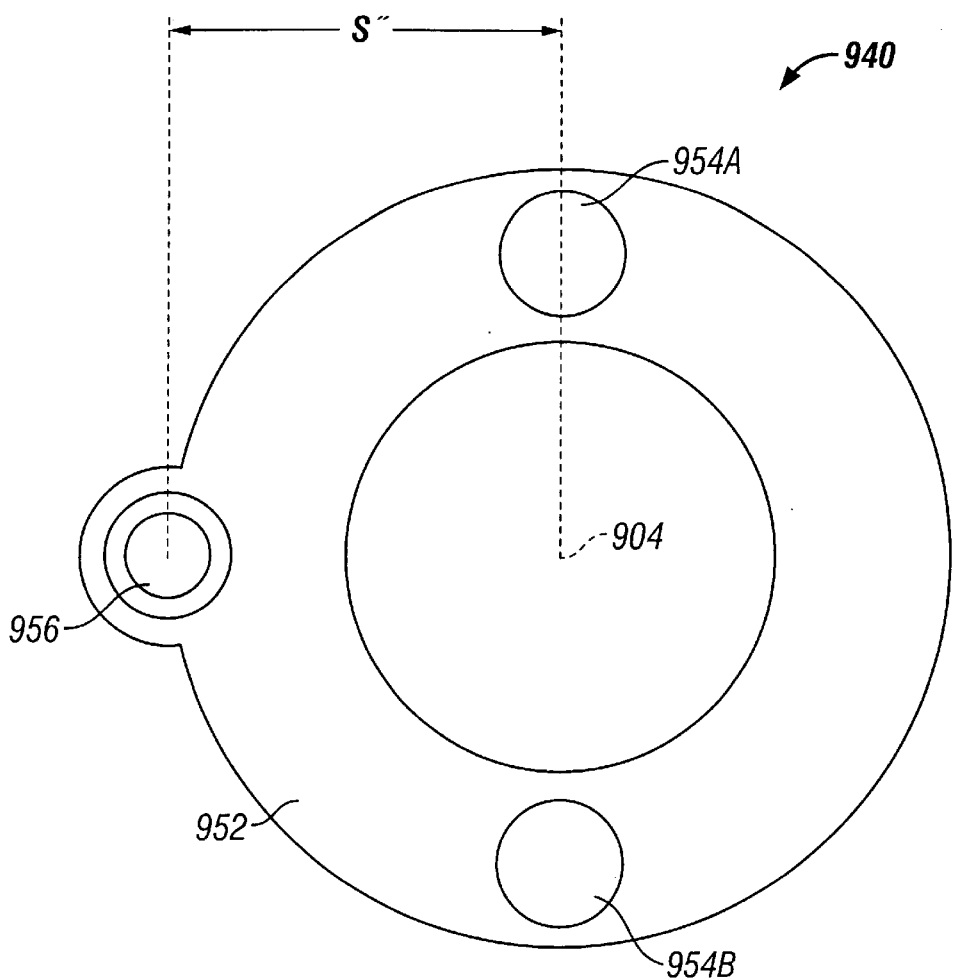
Figure 21:
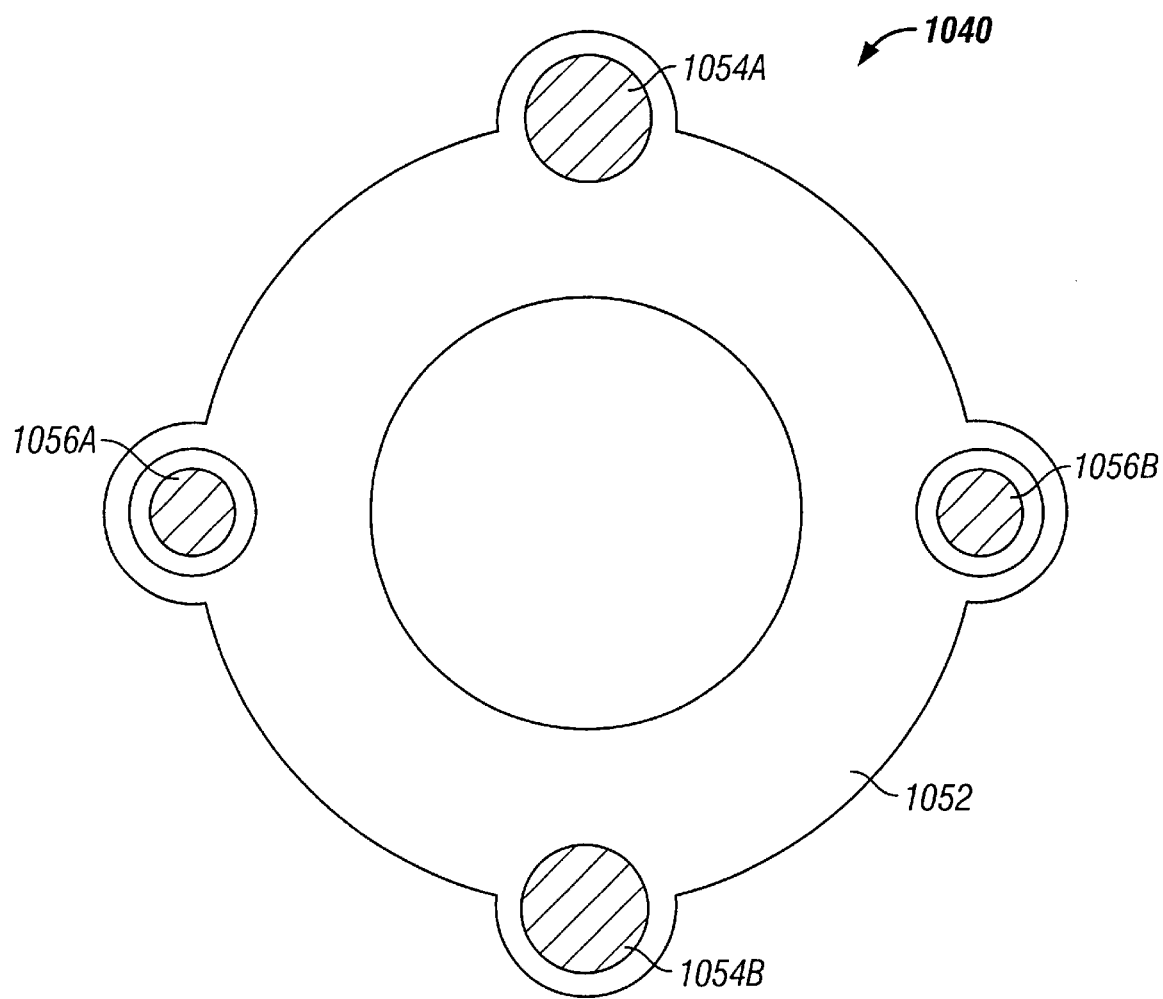

FIGS. 19–21 show transverse sectional views of alternative cross-sections for flexible tip sections. As shown in FIG. 19, a tip 840 may include pull wires 856A and 856B and strengthening members 854A and 854B which intrude into the lumen 834. As the lumen 834 increases in diameter, the thickness of the body 852 decreases and introduces bulges into the lumen 834 at the locations of the pull wires 856A and 856B and strengthening members 854A and 854B. Alternatively, the tip 840 may include a single pull wire. This configuration is useful in applications where a round lumen and thick body are not required.

As shown in FIG. 20, a tip 940 may include a pull wire 956 which protrudes from the outer longitudinal surface of the body 952. By positioning the pull wire 956 farther away from the central axis 904 of the tip 940, the lever arm S" increases in length and so increases the available bending torque, as described above. Alternatively, the tip 940 may include two pull wires on opposite sides of the tip 940. This configuration provides increased torque but sacrifices a round exterior.

As shown in FIG. 21, a tip 1040 may include pull wires 1056A and 1056B and strengthening members 1054A and 1054B which protrude from the body 1052. Similar to the tip 940 shown in FIG. 20, the tip 1040 shown in FIG. 21 has an increased lever arm as well as an increased width between the strengthening members 1054A and 1054B, thereby providing improved lateral stability. Alternatively, the tip 1040 may include a single pull wire. This configuration also provides increased bending torque as described above, but does not provide a round exterior.

Figure 22A:
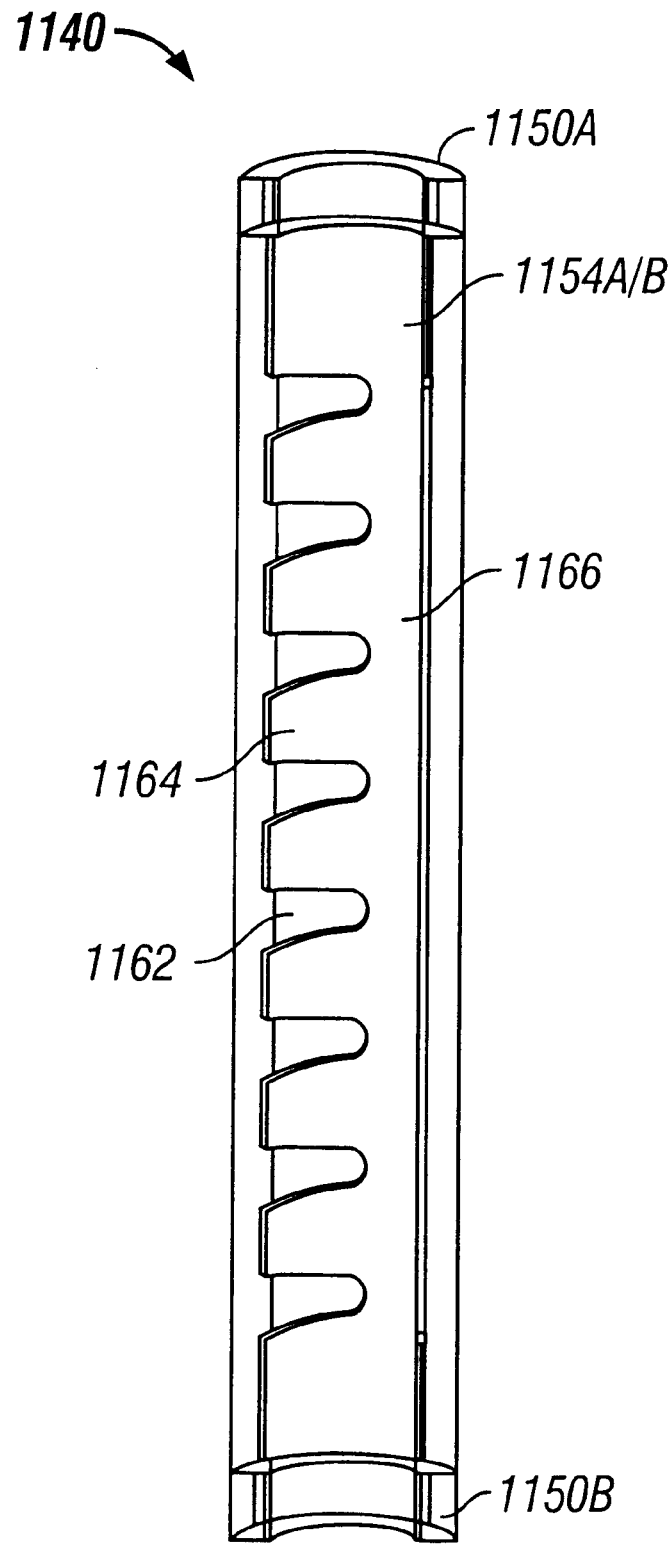
FIGS. 22A to 22G are views of an alternative cannula tip including ribbed strengthening members.
Figure 22B:
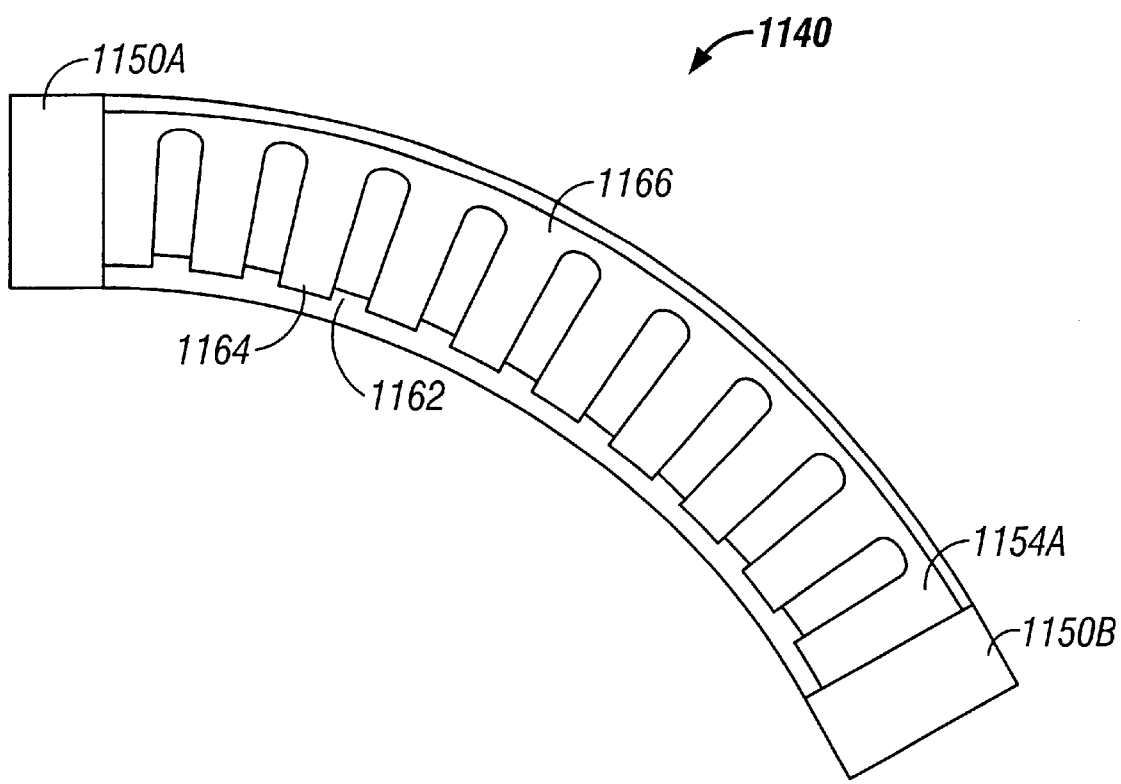
Figure 22C:
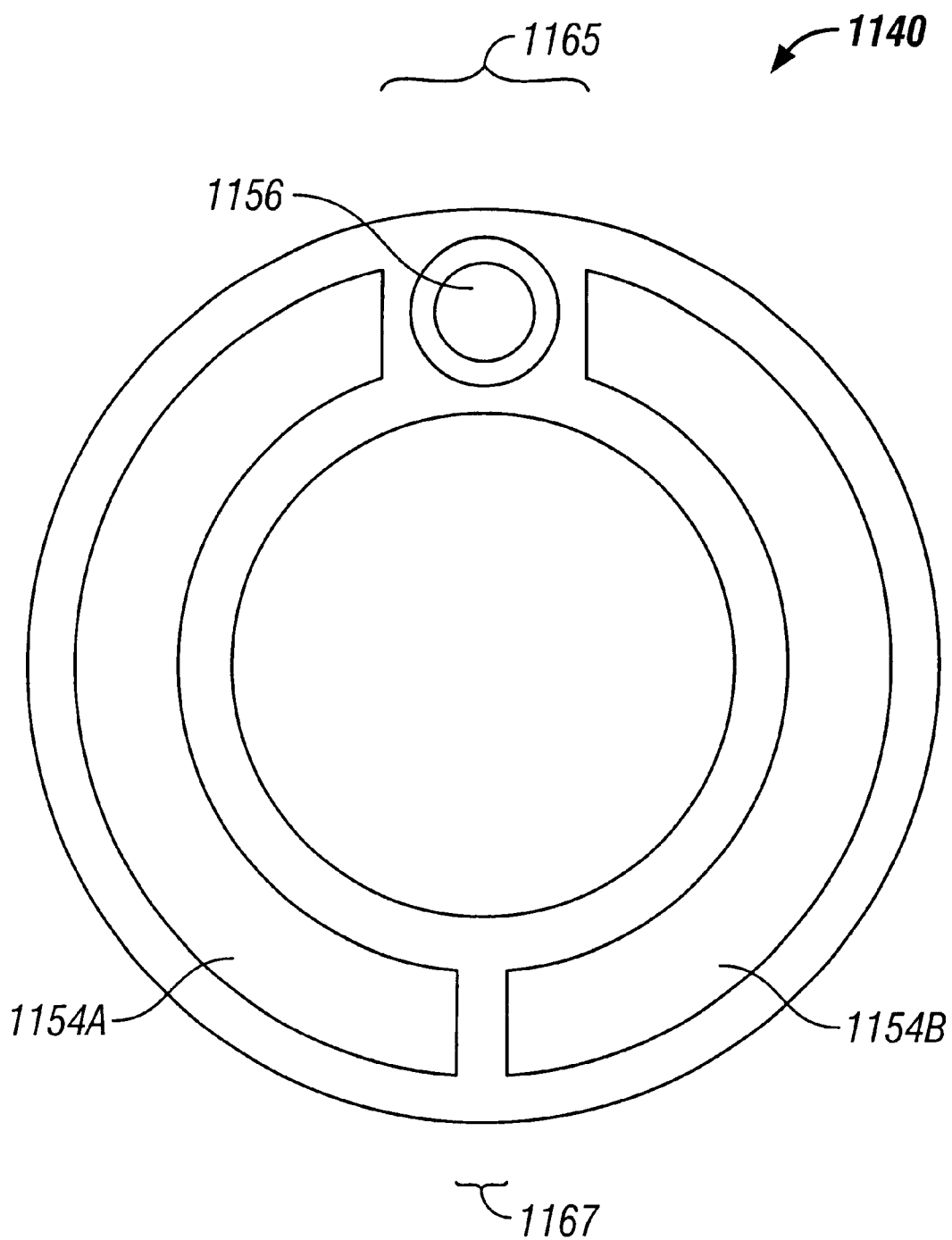
Figure 22D:
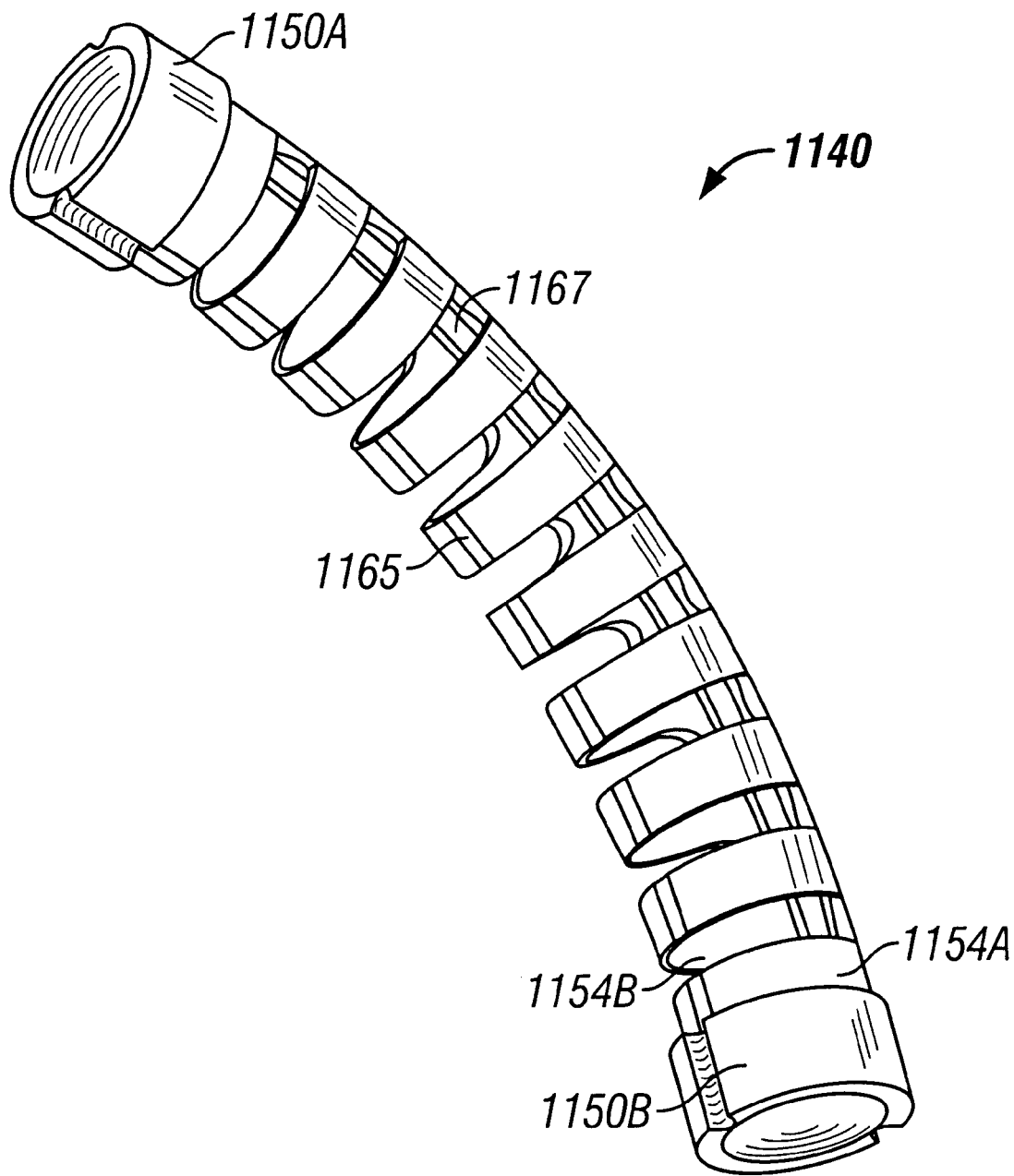
Figure 22E:
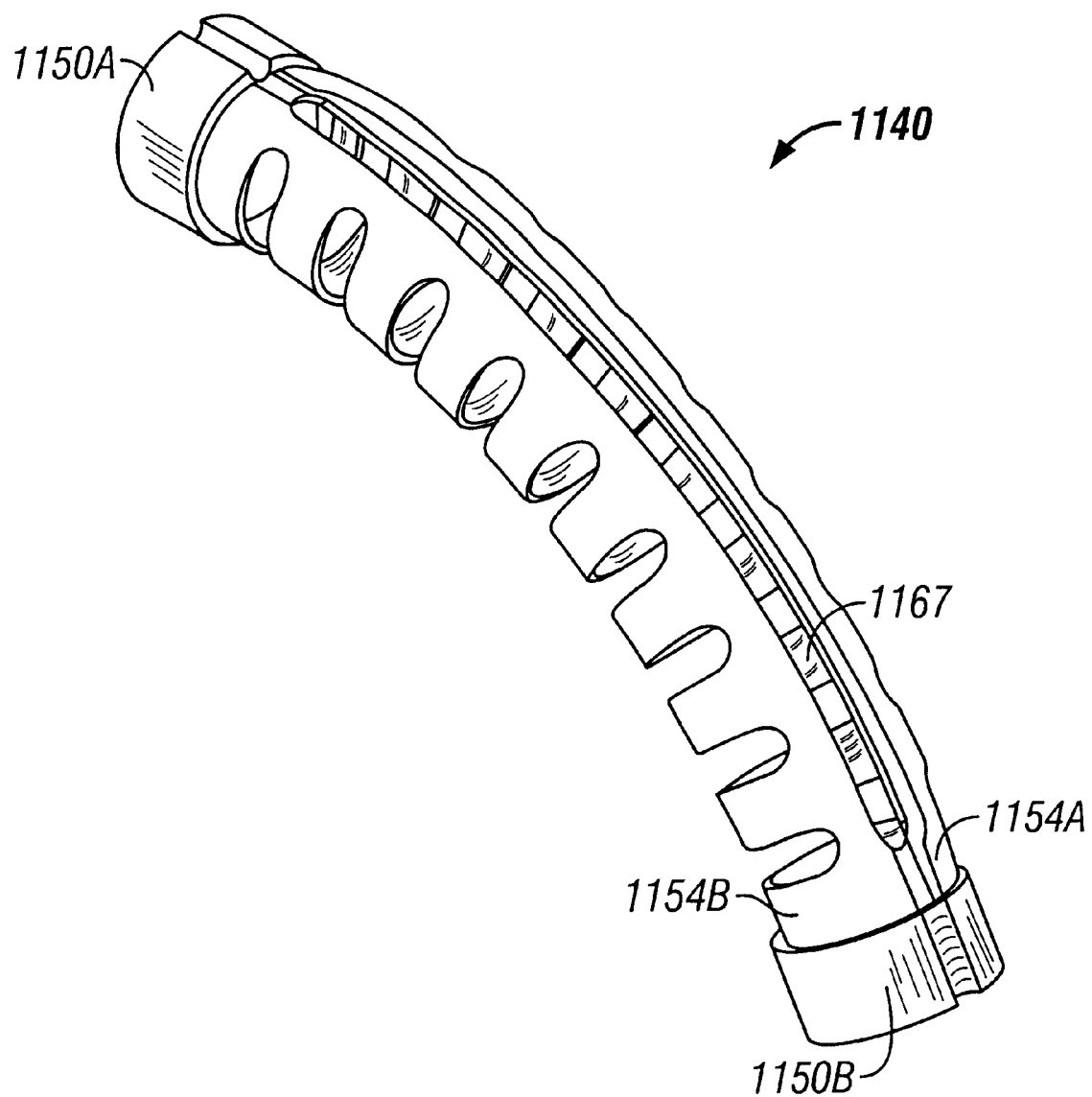
Figure 22F:
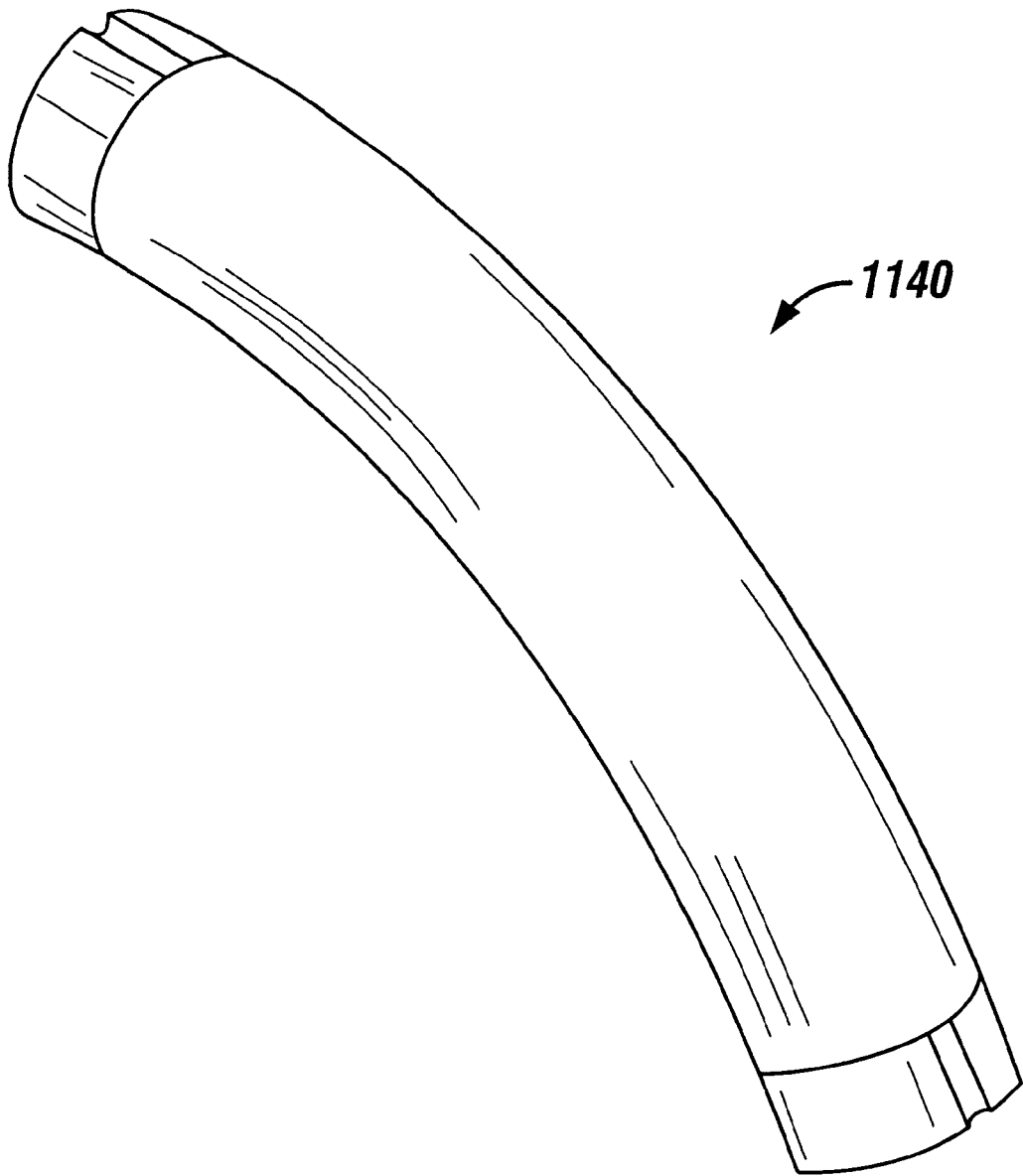
Figure 22G:
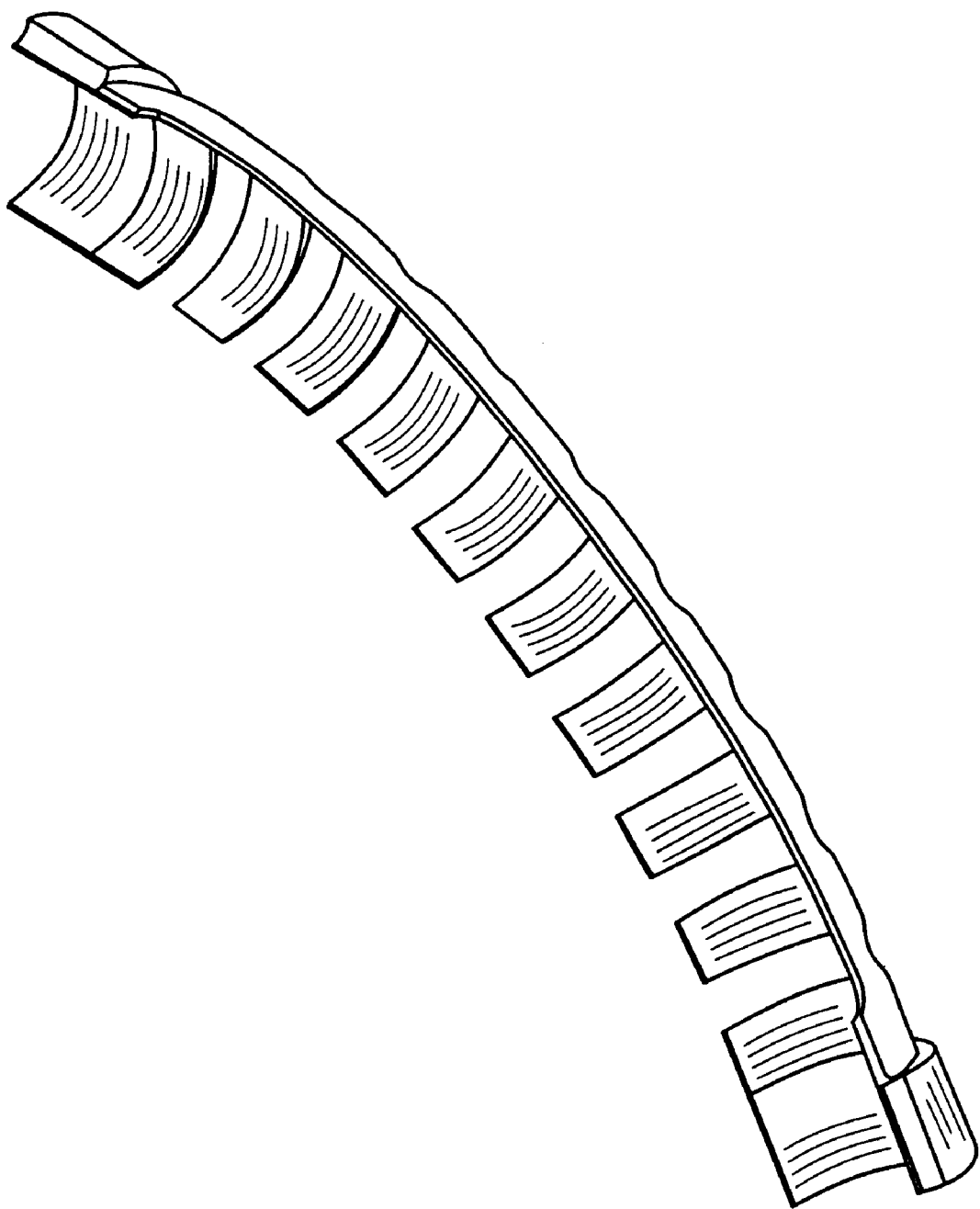
Figure 22H:
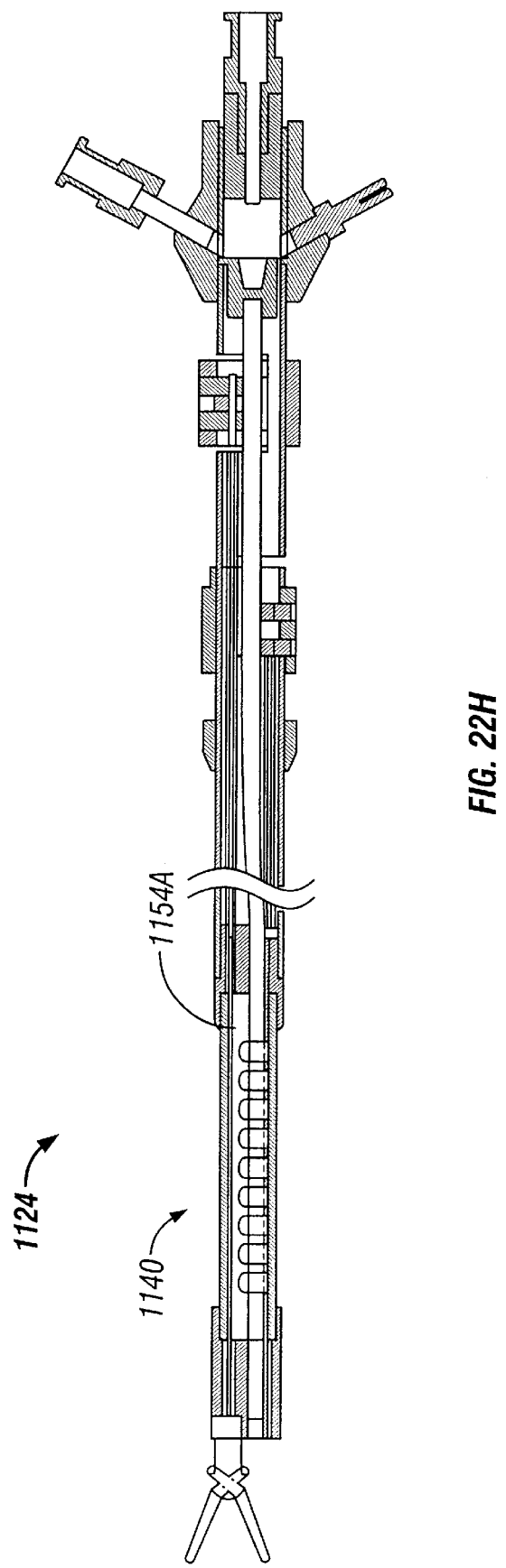
FIG. 22H is a longitudinal view of a cannula which has an alternative cannula tip including ribbed strengthening members.

FIGS. 22A to 22G are views of an alternative cannula tip 1140 including ribbed strengthening members 1154A and 1154B. The tip 1140 may include notched or ribbed longitudinal strengthening members 1154A and 1154B, shown in longitudinal profile in a straight position in FIG. 22A and in a bent position in FIG. 22B, in transverse cross-section in FIG. 22C, and in perspective in FIGS. 22D to 22G. FIG. 22H shows a cannula 1124 including such a tip 1140. The ribbed strengthening members 1154A and 1154B include depressions 1162, leaving ribs 1164 and a backbone 1166. The depressions 1162 are formed so that the ribs 1164 extend toward a pull wire 1156. The ribs 1164 provide radial support for the tip 1140 and increased transverse crush strength. The ribs 1164 preferably are not a necessary part of the ribbed strengthening members 1154A and 1154B for altering the flexibility of the tip 1140. Thus, in an alternative embodiment, the strengthening members 1154A and 1154B may be formed without the ribs 1164, leaving only the backbone 1166. The ribbed strengthening members 1154A and 1154B are attached to collars 1150A and 1150B.

The flexibility of the ribbed strengthening members 1154A and 1154B varies with the width of the backbone 1166. By varying the depth of the depressions 1162, the width of the backbone 1166 can be altered to provide variable flexibility at different points along the ribbed strengthening members 1154A and 1154B, similar to tapering the thickness of the strengthening members 454A and 454B in FIG. 15.

The ribbed strengthening members 1154A and 1154B preferably share a common backbone 1166 or are positioned adjacent to one another, opposite the pull wire 1156. Alternatively, the ribbed strengthening members 1154A and 1154B can be positioned such that the backbones 1166 are diametrically opposite one another or closer to one another, opposite the pull wire 1156. Thus, the tip 1140 can be formed with the ribbed strengthening members 1154A and 1154B positioned similarly to the strengthening members shown in FIG. 3 or FIG. 7, with ribs 1164 extending toward the pull wire 1156. Alternatively, the tip 1140 may include two pull wires 1156, diametrically opposed, to provide bi-directional deflection. In such a case, the backbone 1166 may have ribs 1164 extending in both transverse directions. The positions of the backbones 1166 of the ribbed strengthening members 1154A and 1154B determine the flexibility of the tip 1140.

Where the ribbed strengthening members 1154A and 1154B are close to one another, or have a common backbone 1166, a groove 1167 is preferably formed along the backbones 1166. This backbone groove 1167 provides a channel along the tip 1140, such as for a control wire passing though the tip 1140 to the instrument 28 (not shown). Similarly, where the ribs 1164 are joined or close to one another, a groove 1165 is preferably formed along the tips of the ribs 1164. This rib groove 1165 also provides space for a channel along the tip 1140, such as for the pull wire 1156. The rib groove 1165 and the backbone groove 1167 can be different widths in different embodiments to provide different amounts of space.

Figure 23A:
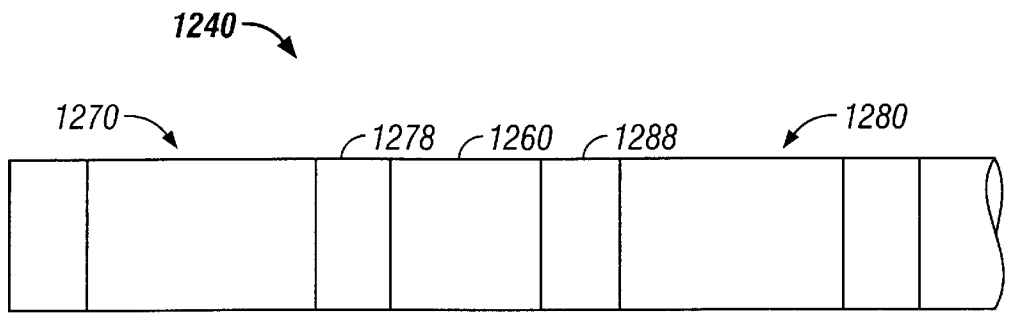
FIGS. 23A to 23C are longitudinal views of an alternative cannula tip including two flexible sections according to the invention.
Figure 23B:
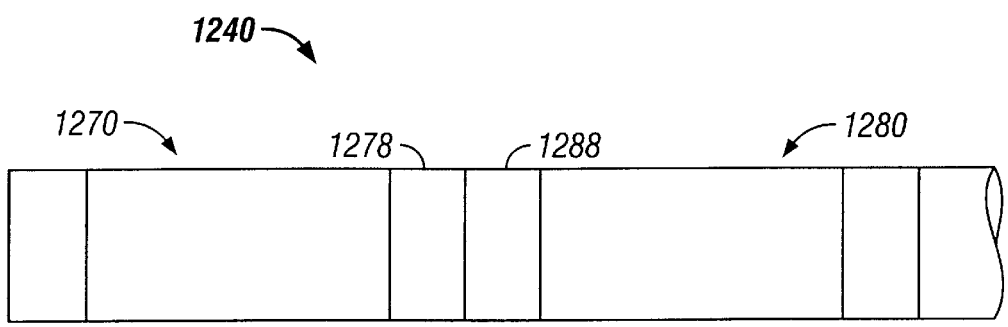
Figure 23C:
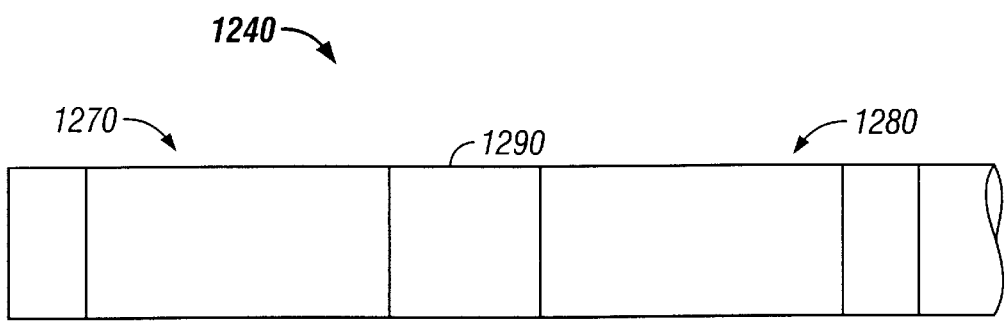

FIGS. 23A to 23C are longitudinal views of an alternative cannula tip 1240 including two flexible sections 1270 and 1280. The tip 1240 may include a distal flexible section 1270 and a proximal flexible section 1280 mounted in series at the distal end of the cannula 24. The distal flexible section 1270 and proximal flexible section 1280 may be separated by an intermediate section 1260 of rigid material, similar to the distal section 42 of the cannula 24. Intermediate section 1260 connects to a proximal collar 1278 of the distal flexible section 1270 and a distal collar 1288 of the proximal flexible section 1280. Alternatively, intermediate section 1260 may be made of a flexible material. As shown in FIG. 23B, in another alternative embodiment, the proximal collar 1278 of the distal flexible section 1270 and the distal collar 1288 of the proximal flexible section 1280 may be adjoining. Alternatively, as shown in FIG. 23C, the distal flexible section 1270 and proximal flexible section 1280 may be joined with a common collar 1290, replacing the proximal collar 1278 of the distal flexible section 1270 and the distal collar 1288 of the proximal flexible section 1280.

Figure 24:
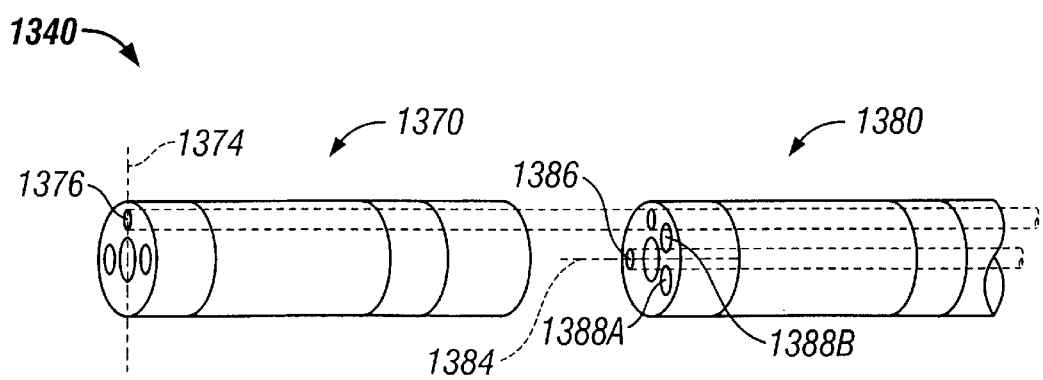
FIG. 24 is a partially exploded view of an alternative cannula tip including two flexible sections according to the invention.

FIG. 24 is a partially exploded view of an alternative cannula tip 1340 including two flexible sections. In a multi-sectional deflected tip 1340, the bending plane 1374 of the distal flexible section 1370 may be orthogonal to the bending plane 1384 of the proximal flexible section 1380. To permit the pull wire 1376 for the distal flexible section 1370 to pass through the proximal flexible section 1380, a configuration such as that shown in FIG. 7 is particularly useful for the proximal flexible section 1380 as the pull wire 1376 of the distal flexible section 1370 does not interfere with the strengthening members 1388A and 1388B of the proximal flexible section 1380. Such a configuration permits greater maneuverability which may be useful for guiding an instrument around obstacles. Alternatively, the bending planes 1374 and 1384 may be in the same plane, allowing the tip 1340 to perform wider deflections or to controllably rack if the pull wires 1376 and 1386 are on opposite sides of the tip 1340.

Figure 25:
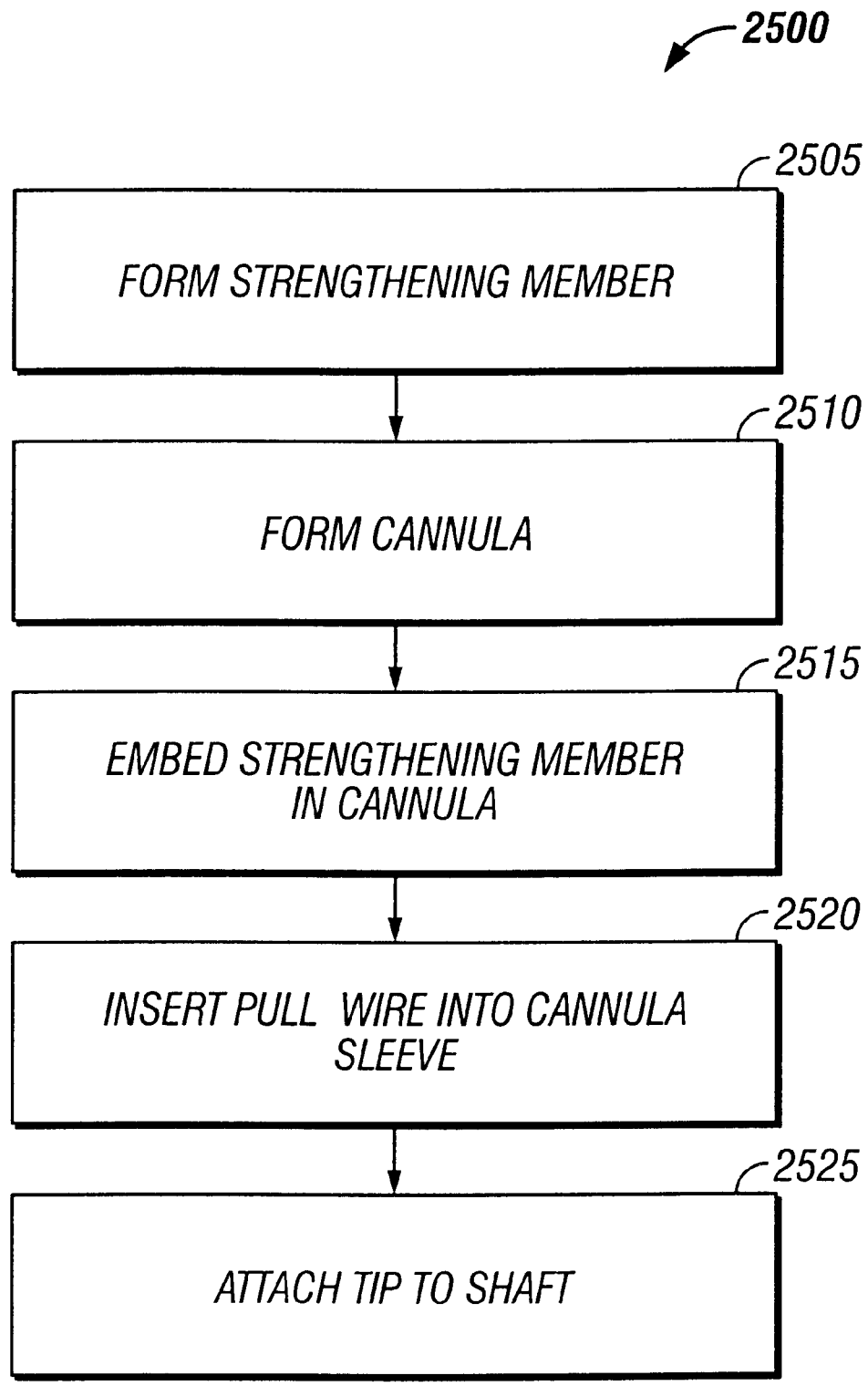
FIG. 25 is a flowchart of a process of manufacturing a cannula having a steerable tip.

FIG. 25 is a flowchart of a process (2500) of manufacturing a cannula having a steerable tip. One or more strengthening members are formed, such as by injection molding a single strengthening member using a plastic material such as ULTEM (2505). The molded strengthening member incorporates collars at ends of the strengthening member in a single piece. Alternatively, the strengthening member may be machined using standard machining practices (e.g., using a cutting tool such as a boring bar). In another implementation, strengthening members can be formed as two or more pieces (e.g., distal and proximal end caps and a backbone section) and bonded together. As described above, the strengthening members can be formed having one or more grooves. A cannula having a lumen and a sleeve for a pull wire is formed by overmolding (2510). The strengthening member is placed into a second injection molding tool and an outer elastomeric tube is over molded around the strengthening member, forming a composite structure with the strengthening member embedded therein (2515). Alternatively, the strengthening member can be placed into a casting tool and the cannula can be cast into place around the strengthening member. Upon removal from the overmolding tool, a pull wire is inserted into the sleeve of the cannula (2520). Alternatively, the sleeve can be machined after the cannula has been formed. The resulting tip structure is then attached to a rigid shaft element (2525) (recall base section 42 of FIG. 1). The order of these manufacturing steps are illustrative and may vary.

Alternatives to molding the body of the flexible section over the strengthening members and pull wire(s) include a variety of extrusion and coextrusion techniques. Such techniques may include forming the body and strengthening members as a unit and then securing them to proximal and distal collars. A key advantage of such manufacturing processes is that they facilitate the economical provision of flexible tip sections of different lengths.

In one process of manufacturing the cannula 24 shown in FIG. 2, the proximal collar 50A and distal collar 50B are provided such as by molding the illustrated shapes from a substantially rigid thermoplastic material (e.g., ULTEM). Alternatively, the collars 50A and 50B may be machined from a suitable biocompatible material. The strengthening members 54A and 54B may then be affixed to the collars 50A and 50B. Alternatively, the end collars 50A and 50B are formed unitarily with the strengthening members 54A and 54B (e.g., by molding or machining). The sleeve 58 may optionally be placed between the collars. Additionally, at this point, the pull wire may be threaded through the proximal collar 50A and sleeve 58 (if present) and secured to the distal collar 50B. In the preferred embodiment, the resulting assembly is placed in a mold and the body 52 is molded around the assembly. Suitable elastomeric material for the body 52 may include silicone or latex rubber, polyurethane, or any other appropriate biocompatible material having suitable flexibility and water/gas-tightness. In the illustrated embodiment, the pull wire 56 and strengthening members 54A and 54B may be formed of multi-stranded steel wire. Optionally, the pull wire 56 may be formed of a strong single strand wire or of another material with high tensile strength, such as aramid fiber. Optionally, the strengthening members 54A and 54B may be formed of a tightly coiled wire or as a flexible rod. The sleeve 58 may be formed of a loosely coiled steel wire and serves to prevent the pull wire 56 from cutting into the body 52 beyond the sleeve 58.

In one process of manufacturing the cannula tip 1140 shown in FIGS. 22A to 22G, the ribbed strengthening members 1154A and 1154B are injection molded using a plastic material such as Ultem. The molded ribbed strengthening members 1154A and 1154B incorporate the end caps and the ribs 1164 in a single piece. Alternatively, the ribbed strengthening members 1154A and 1154B may be machined using standard machining practices as a unitary piece (e.g., using a cutting tool such as a reamer). In another implementation, the ribbed strengthening members 1154A and 1154B can be machined as two or more pieces (e.g., distal and proximal end caps and a backbone section) and bonded together. The ribbed strengthening members 1154A and 1154B are then placed into a second injection molding tool and over molded with the elastomeric outer tube thus forming a composite structure. Alternatively, the ribbed strengthening members 1154A and 1154B can be placed into a casting tool and the outer elastomeric tube can be cast into place forming a composite structure. Upon removal from the overmolding tool, the composite tip structure 1140 is then attached to a rigid shaft element (recall base section 42 of FIG. 1).

A number of embodiments of the present invention have been described. Nevertheless, it will be understood that various modifications may be made without departing from the spirit and scope of the invention. For example, various lumen configurations may be provided and various manufacturing techniques may be employed. Accordingly, other embodiments are within the scope of the following claims.

What is claimed is:

1. A steerable probe comprising:
   (a) a cannula having:
      (1) a proximal end and a distal end and extending along a length therebetween;
      (2) an exterior surface;
      (3) an interior surface defining a lumen;
      (4) an elongate flexible section extending along a first portion of the length and having a section proximal end and a section distal end;
   (b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end; and
   (c) at least two longitudinal strengthening members, extending along and embedded in said flexible section generally opposite each other about the preferred bending plane; wherein the flexible section is precurved in a second direction opposite the first direction.

2. A steerable probe comprising:
   (a) a cannula having:
      (1) a proximal end and a distal end and extending along a length therebetween;
      (2) an exterior surface;
      (3) an interior surface defining a lumen;
      (4) an elongate flexible section extending along a first portion of the length and having a section proximal end and a section distal end;
   (b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end; and
   (c) at least two longitudinal strengthening members, extending along and embedded in said flexible section generally opposite each other about the preferred bending plane;

wherein the longitudinal strengthening members each comprise a coiled wire surrounding a core wire.

3. A steerable probe comprising:
(a) a cannula having:
    (1) a proximal end and a distal end and extending along a length therebetween;
    (2) an exterior surface;
    (3) an interior surface defining a lumen;
    (4) an elongate flexible section extending along a first portion of the length and having a section proximal end and a section distal end;
(b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end; and
(c) at least two longitudinal strengthening members, extending along and embedded in said flexible section generally opposite each other about the preferred bending plane;
wherein the longitudinal strengthening members each comprise a coiled wire.

4. A steerable probe comprising:
(a) a cannula having:
    (1) a proximal end and a distal end and extending along a length therebetween;
    (2) an exterior surface;
    (3) an interior surface defining a lumen;
    (4) an elongate flexible section extending along a first portion of the length and having a section proximal end and a section distal end;
(b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end; and
(c) at least two longitudinal strengthening members, extending along and embedded in said flexible section generally opposite each other about the preferred bending plane;
wherein the longitudinal strengthening members each include:
(a) a backbone; and
(b) one or more ribs extending from the backbone toward the pull wire.

5. The probe of claim 4, wherein the backbones of the longitudinal strengthening members are connected.

6. The probe of claim 4, wherein the ribs provide radial support to the cannula.

7. The probe of claim 4, wherein the ribs are not all the same length.

8. A steerable probe comprising:
(a) a cannula having:
    (1) a proximal end and a distal end and extending along a length therebetween;
    (2) an exterior surface;
    (3) an interior surface defining a lumen;
    (4) an elongate flexible section extending along a first portion of the length and having a section proximal end and a section distal end;
(b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end;
(c) at least two longitudinal strengthening members, extending along and embedded in said flexible section generally opposite each other about the preferred bending plane; and
a second pull wire and wherein the cannula further comprises a second flexible section extending along a second portion of the length of the cannula and having a second section proximal end and a second section distal end, the second pull wire positioned so that pulling on the second pull wire deflects the second flexible section transverse to the first direction.

9. A steerable probe comprising:
(a) a cannula having:
    (1) a proximal end and a distal end and extending along a length therebetween;
    (2) an exterior surface;
    (3) an interior surface defining a lumen;
    (4) an elongate flexible section extending along a first portion of the length and having a section proximal end and a section distal end;
(b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end;
(c) at least two longitudinal strengthening members, extending along and embedded in said flexible section generally opposite each other about the preferred bending plane;
wherein the elongate flexible section further includes a distal annular stiffener at the section distal end and a proximal annular stiffener at the section proximal end; and
wherein the first longitudinal strengthening member, second longitudinal strengthening member, distal annular stiffener, and proximal annular stiffener are unitarily formed.

10. A steerable probe comprising:
(a) a cannula having:
    (1) a proximal end and a distal end and extending along a length therebetween;
    (2) an exterior surface;
    (3) an interior surface defining a lumen;
    (4) an elongate flexible section extending along a first portion of the length and having a section proximal end and a section distal end;
(b) a pull wire for deflecting said flexible section in a first direction in a preferred bending plane, the pull wire substantially embedded in the cannula between the interior surface and the exterior surface and extending from the section proximal end to the section distal end, the pull wire secured to the cannula adjacent the section distal end and freely passing through the section proximal end; and
(c) at least two longitudinal strengthening members, extending along and embedded in said flexible section generally opposite each other about the preferred bending plane;

wherein the cannula further comprises an inner sleeve and wherein the inner sleeve, first longitudinal strengthening member, and second longitudinal strengthening member are unitarily formed.

11. A method of manufacturing a steerable probe comprising:
 (a) forming at least one strengthening member from a first material;
 (b) forming a cannula from a second material, wherein the cannula includes a sleeve and a lumen;
 (c) embedding each strengthening member longitudinally in the cannula; and
 (d) inserting a pull wire into the sleeve, wherein at least a portion of the cannula deflects in response to tension being applied to the pull wire;
 wherein each strengthening member is formed by injection molding so that all at least one strengthening members form a unitary piece, and the cannula is formed by overmolding around the unitary piece.

12. A method of manufacturing a steerable probe comprising:
 (a) forming at least one strengthening member from a first material;
 (b) forming a cannula from a second material, wherein the cannula includes a sleeve and a lumen;
 (c) embedding each strengthening member longitudinally in the cannula; and
 (d) inserting a pull wire into the sleeve, wherein at least a portion of the cannula deflects in response to tension being applied to the pull wire;
 wherein each strengthening member includes a backbone and one or more ribs extending from the backbone toward the pull wire.

* * * * *